(12) United States Patent
Lacasse et al.

(10) Patent No.: US 10,828,319 B2
(45) Date of Patent: Nov. 10, 2020

(54) CHITOSAN HYDROGELS FOR ACCELERATING INVOLUTION AND PREVENTING INFECTION OF THE MAMMARY GLAND AT DRYING-OFF

(71) Applicant: HER MAJESTY THE QUEEN IN RIGHT OF CANADA, AS REPRESENTED BY THE MINISTER OF AGRICULTURE AND AGRI-FOOD, Sherbrooke (CA)

(72) Inventors: Pierre Lacasse, Sherbrooke (CA); Samuel Lanctôt, Sherbrooke (CA); Patrick Fustier, St-Hyacinthe (CA); André Bégin, Sherbrooke (CA); Ali R. Taherian, St-Hyacinthe (CA); Barbara Bisakowski, St-Hyacinthe (CA)

(73) Assignee: HER MAJESTY THE QUEEN IN RIGHT OF CANADA, AS REPRESENTED BY THE MINISTER OF AGRICULTURE AND AGRI-FOOD, Sherbrooke (CA)

( * ) Notice: Subject to any disclaimer, the term of this patent is extended or adjusted under 35 U.S.C. 154(b) by 0 days.

(21) Appl. No.: 16/085,691

(22) PCT Filed: Mar. 16, 2017

(86) PCT No.: PCT/CA2017/050339
§ 371 (c)(1),
(2) Date: Sep. 17, 2018

(87) PCT Pub. No.: WO2017/156632
PCT Pub. Date: Sep. 21, 2017

(65) Prior Publication Data
US 2019/0060352 A1 Feb. 28, 2019

Related U.S. Application Data

(60) Provisional application No. 62/310,025, filed on Mar. 18, 2016.

(51) Int. Cl.
| | | |
|---|---|---|
| A61K 31/722 | (2006.01) | |
| C08L 5/08 | (2006.01) | |
| C08B 37/08 | (2006.01) | |
| A61P 31/00 | (2006.01) | |
| A61K 9/00 | (2006.01) | |
| A61K 47/10 | (2017.01) | |
| C08J 3/075 | (2006.01) | |

(52) U.S. Cl.
CPC .......... *A61K 31/722* (2013.01); *A61K 9/0019* (2013.01); *A61K 9/0041* (2013.01); *A61K 47/10* (2013.01); *A61P 31/00* (2018.01); *C08B 37/003* (2013.01); *C08L 5/08* (2013.01); *C08J 3/075* (2013.01)

(58) Field of Classification Search
None
See application file for complete search history.

(56) References Cited

U.S. PATENT DOCUMENTS

| | | | |
|---|---|---|---|
| 6,344,488 B1 * | 2/2002 | Chenite | A61K 9/0019 |
| | | | 514/777 |
| 2005/0191270 A1 | 9/2005 | Gruening et al. | |
| 2010/0151029 A1 | 6/2010 | Gruening et al. | |
| 2017/0119785 A1 | 5/2017 | Rajagopalan et al. | |

FOREIGN PATENT DOCUMENTS

| | | | | |
|---|---|---|---|---|
| CA | 2212300 A1 | 2/1999 | | |
| EP | 1448607 A1 | 8/2004 | | |
| IN | 1668MUM2009 A | * | 1/2012 | ............ A61K 31/00 |
| WO | 9907416 A1 | 2/1999 | | |
| WO | WO-2015093937 A1 | * | 6/2015 | ............ C12R 1/225 |
| WO | 2017079216 A1 | 5/2017 | | |

OTHER PUBLICATIONS

Oliver, S. P., & Smith, K. L. (1982). Bovine mammary involution following intramammary infusion of colchicine and endotoxin at drying off. Journal of Dairy Science, 65(5), 801-813. (Year: 1989).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Dang, Q. F., Yan, J. Q., Lin, H., Chen, X. G., Liu, C. S., Ji, Q. X., & Li, J. J. (2012). Design and evaluation of a highly porous thermosensitive hydrogel with low gelation temperature as a 3D culture system for Penaeus chinensis lymphoid cells. Carbohydrate polymers, 88(1), 361-368. (Year: 2012).*
Aliaghaie, M., Mirzadeh, H., Dashtimoghadam, E., & Taranejoo, S. (2012). Investigation of gelation mechanism of an injectable hydrogel based on chitosan by rheological measurements for a drug delivery application. Soft Matter, 8(27), 7128-7137. (Year: 2012).*
Sordillo, L. M., Nickerson, S. C., Akers, R. M., & Oliver, S. P. (1987). Secretion composition during bovine mammary involution and the relationship with mastitis. The International journal of biochemistry, 19(12), 1165-1172. (Year: 1987).*
Bucke, C. (Ed.). (1999). Carbohydrate biotechnology protocols (vol. 10). Springer Science & Business Media. (Year: 1999).*
Chenite, A., et al., "Novel injectable neutral solutions of chitosan form biodegradable gels in situ." Biomaterials, 2000, 21: 2155-2161.

(Continued)

*Primary Examiner* — Dale R Miller
(74) *Attorney, Agent, or Firm* — Saliwanchik, Lloyd & Eisenschenk

(57) ABSTRACT

A method of preventing intramammary infection and accelerating involution by administration of a biological response modifier, specifically a chitosan solution, to the teat of a lactating mammal at drying-off A chitosan solution neutralized with a weak base such as β-glycerophosphate can remain liquid at room temperature for injection into a teat, but can form a hydrogel at body temperature inside the teat. The neutralized chitosan solution can also be optionally co-administered with a teat sealant.

17 Claims, 10 Drawing Sheets
Specification includes a Sequence Listing.

(56) References Cited

OTHER PUBLICATIONS

Chenite, A., et al., "Rheological characterisation of thermogelling chitosan/glycerol-phosphate solutions." Carbohydrate Polymers, 2001, 46: 39-47.
Dallard, B.E., et al., "The effect of a single intramammary infusion of a biological response modifier in cows at drying off." Vet Res Commun, 2010, 34: 519-532.
Lanctôt, S., et al., "Effect of intramammary infusion of chitosan hydrogels at drying-off on bovine mammary gland involution." J. Dairy Sci., 2017, 100: 2269-2281.
Moon, J.-S., et al., "The antibacterial and immunostimulative effect of chitosan-oligosaccharides against infection by *Staphylococcus aureus* isolated from bovine mastitis." Appl Microbiol Biotechnol, 2007, 75: 989-998.
Taherian, A.R., et al., "Rheological and thermogelling properties of commercials chitosan/β-glycerophosphate: Retention of hydrogel in water, milk and UF-milk." Food Hydrocolloids, 2017, 63: 635-645.
Zecconi, A., et al., "Efficacy of a Biological Response Modifier in Preventing *Staphylococcus aureus* Intramammary Infections After Calving." J Dairy Sci, 1999, 82: 2101-2107.
Zhou, H.Y., et al., "Glyvrtophosphate-based chitosan thermosensitive hydrogels and their biomedical applications." Carbohydrate Polymers, 2015, 117: 524-536.
Rajagopalan, S., et al., U.S. Appl. No. 62/250,126, filed Nov. 3, 2015; "Sol-Gel Polymer Composites." First Priority document for WO 2017/079216 A1, as cited on Extended European Search Report for EP 17765617.0.

\* cited by examiner

CHITOSAN HYDROGELS FOR ACCELERATING INVOLUTION AND PREVENTING INFECTION OF THE MAMMARY GLAND AT DRYING-OFF

CROSS REFERENCE TO A RELATED APPLICATION

This application is a National Stage Application of International Application Number PCT/CA2017/050339, filed Mar. 16, 2017; which claims the benefit of U.S. Provisional Application Ser. No. 62/310,025, filed Mar. 18, 2016; both of which are incorporated herein by reference in their entirety.

BACKGROUND

The present application is directed to methods for preventing infection of mammary glands. In particular, the present application is directed to methods for accelerating involution and preventing infection of mammary glands of dairy cows after milking is ceased.

The lactation cycle of a dairy cow should include a dry period before the end of a pregnancy, during which the animal stops milk production. This allows the animal to rest and regenerate its mammary cells prior to the birth of the next offspring, so that milk production is optimized in the next lactation. The dry period is initiated by "drying off" the animal. In general, milking of the animal is stopped abruptly, so that the back pressure of milk accumulating in the udder can stimulate mammary cells to stop producing milk. The animal may also be given a high fibre, low calorie diet during the drying-off period to encourage the cessation of milk production. However, animals being dried off have an increased risk of intramammary infections (IMIs).

During drying-off, the mammary gland undergoes a period of active involution during which mammary tissue regresses and ceases milk secretion. As involution is completed, a keratin plug often forms in the teat to provide a physical barrier to bacterial entry, and the number of immune cells in the mammary secretions increases, providing a further defense against infection. Consequently, when early involution of the mammary gland is completed, the risk of acquiring a new IMI is minimal. However, the animal is highly susceptible to IMIs during the early involution period, especially if milk yields are high at the time of drying-off. Milk accumulation and leakage through the teats can impair the formation of a keratin plug, allowing microorganisms to gain entry to the mammary gland. Moreover, mammary gland secretions contain few immune cells at the beginning of involution, and high fat and casein concentrations in mammary gland secretions can interfere with the ability of the immune cells that are present to defend against such microorganisms. Therefore, it is important to implement an efficient control program during this period to prevent IMIs and the resulting inflammation (mastitis).

Treatment of animals with antibiotics at the end of lactation is commonly practiced, and helps to cure existing IMIs and prevent new infections. Alternative methods of preventing and treating IMIs include the use of internal teat sealants to prevent access to mammary tissue by pathogenic microorganisms, and external teat dipping using iodine-based disinfectant teat dips. However, these methods have drawbacks. Antibiotic treatment may not be equally effective against all pathogens, and there is a risk of antibiotic contamination of milk if the dry period is not long enough to permit adequate clearance of the antibiotic from the animal prior to the subsequent lactation period. Furthermore, blanket antibiotic treatment of animals regardless of their infection status is negatively perceived by consumers. However, selective antibiotic treatment of only those animals at high risk of infection necessitates the use of alternative methods for prevention of infections in untreated animals, such as inert bismuth-based teat sealants, which are not totally effective, and external teat dipping, which is labour-intensive and difficult to implement in a free-stall operation.

The innate immunity of the mammary gland is an important defense against infection by pathogens that manage to gain entry to the gland via the teat canal, despite physical barriers to teat entry, such as a keratin plug or a teat sealant. Leukocytes (white blood cells), especially neutrophils and macrophages, are important components of the innate immunity, and constitute a high proportion of somatic cells found in milk. The Furstenberg's rosette, a structure strategically located at the internal end of the streak canal, appears to be a major point of entry of leukocytes, which are thought to leave the teat wall and enter the teat cistern to intercept bacteria before they reach the mammary gland. It has been observed that the presence of a high somatic cell count (SCC) in a quarter can prevent the induction of experimental mastitis in cows. Thus, it appears that stimulating innate immunity and increasing SCC could enhance mammary gland resistance to new IMIs. Furthermore, accelerating the involution process might reduce the period during which an animal being dried off is especially susceptible to infection and further enhance resistance to new IMIs.

Biological response modifiers (BRM) are agents that modify the host's response to pathogens with resultant beneficial prophylactic or therapeutic effects. Although some biological response modifiers, including but not limited to vaccines, act by stimulating the adaptive immunity, other biological response modifiers stimulate the innate immune response, and therefore may improve resistance to IMI. A biological response modifier that will improve the resistance of dairy animals to intramammary infections during the drying-off period is therefore desirable.

Chitosan is a bioactive, biocompatible, biodegradable and nontoxic hydrocolloid, with hemostatic, bacteriostatic, and other properties favourable for a range of industrial and biomedical applications. Chitosan is a polysaccharide comprising 1-4-linked residues of 2-amino-2-deoxy-$\beta$-D-glucose (glucosamine) and 2-acetamido-2-deoxy-$\beta$-D-glucose (N-acetylglucosamine). Chitosan is prepared by at least partial deacetylation of the naturally occurring polysaccharide chitin (poly-N-acetylglucosamine or (1→4)-2-acetamido-2-deoxy-$\beta$-D-glucan), which is found naturally in the shells of insects and crustaceans such as crabs and shrimp, and in the cell walls of fungi. Thus, acetyl groups are removed from at least some of the N-acetylglucosamine residues of chitin to form glucosamine residues.

In commercial preparations of chitosan, usually from about 50% to about 100% of the N-acetylglucosamine residues of chitin have been deacetylated to form glucosamine residues. The deacetylated glucosamine residues have free amino groups which exist, at least partially, in protonated form in aqueous solution at pH values below 6.5. Thus, chitosan dissolves to a significant extent in acidic solution, and soluble chitosan is cationic, allowing it to bind to negatively charged surfaces and biological materials. However, when a solution of chitosan is neutralized by a weak base, the chitosan can form a hydrated, gel-like precipitate. The properties of chitosan can thus be significantly affected by its degree of deacetylation (DDA).

SUMMARY

The present invention provides a composition for accelerating involution or preventing intramammary infection in a lactating mammal at drying-off, the composition containing a biological response modifier and an acceptable carrier. In at least one embodiment, the biological response modifier contains a chitosan hydrogel.

Another aspect of the present invention provides a method of accelerating involution or preventing intramammary infection, including administering a biological response modifier as described herein or a composition thereof to a lactating mammal at drying-off.

Still another aspect of the present invention provides the use of a biological response modifier as described herein or a composition thereof for accelerating involution or preventing intramammary infection in a lactating mammal at drying-off.

BRIEF DESCRIPTION OF THE DRAWINGS

Further features of the present invention will become apparent from the following written description and the accompanying figures, in which.

Figure 7A:
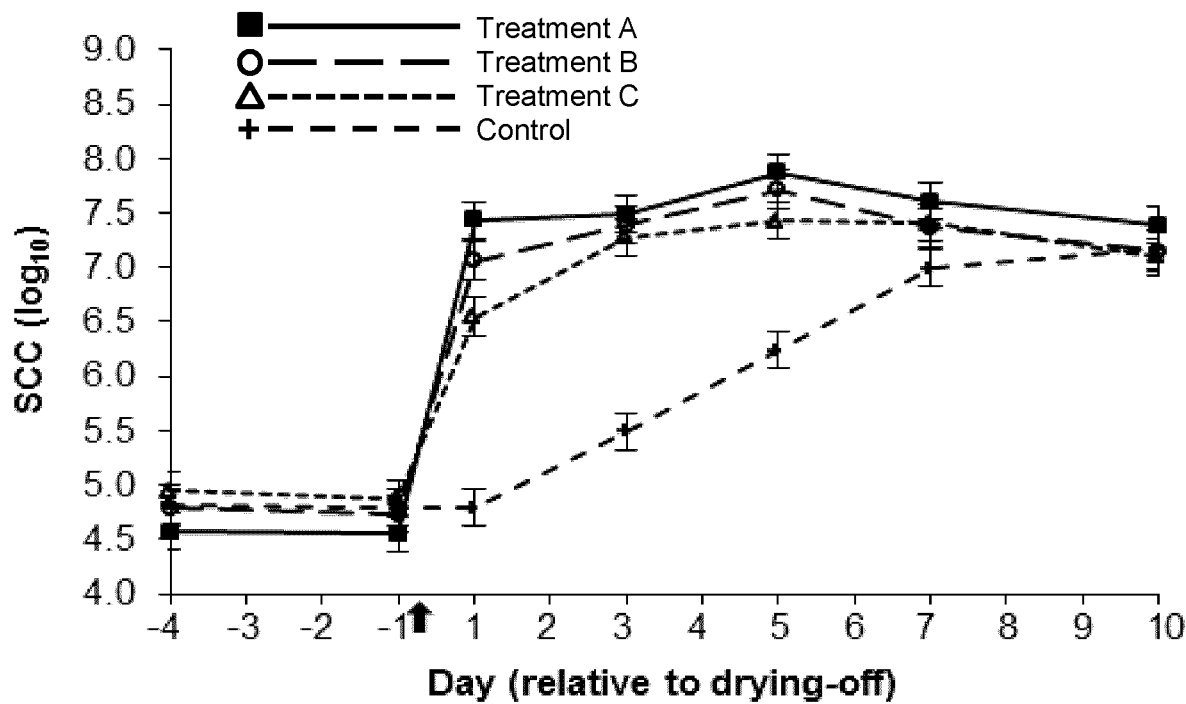
Figure 7B:
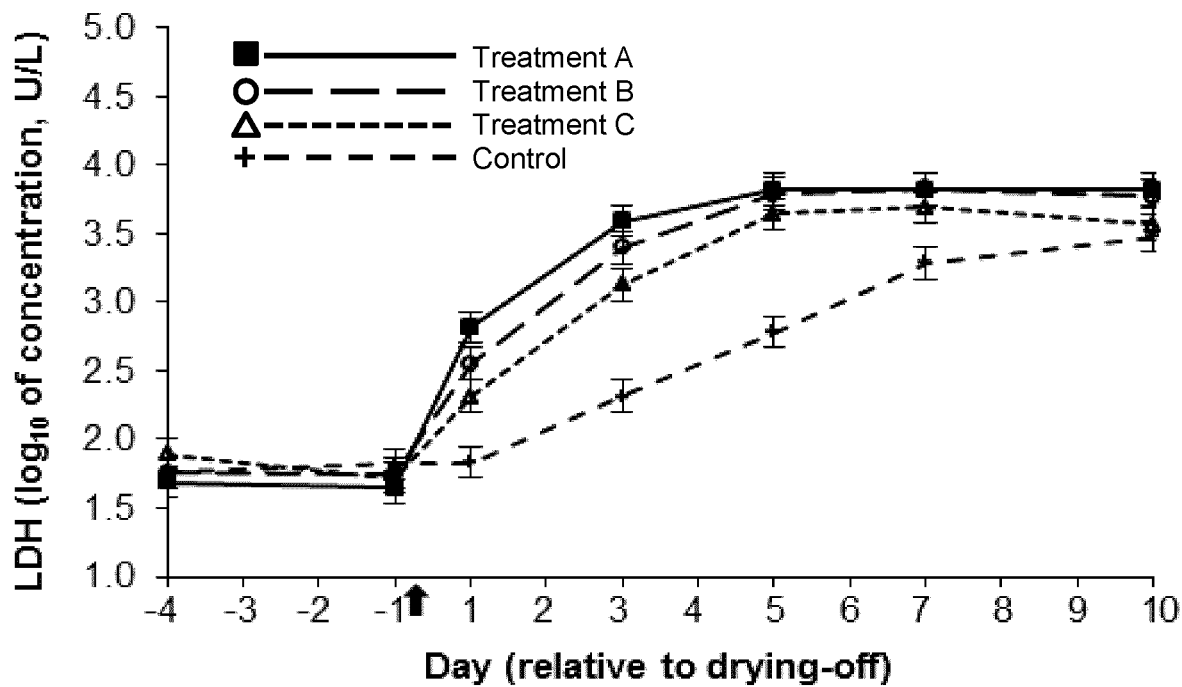
Figure 7C:
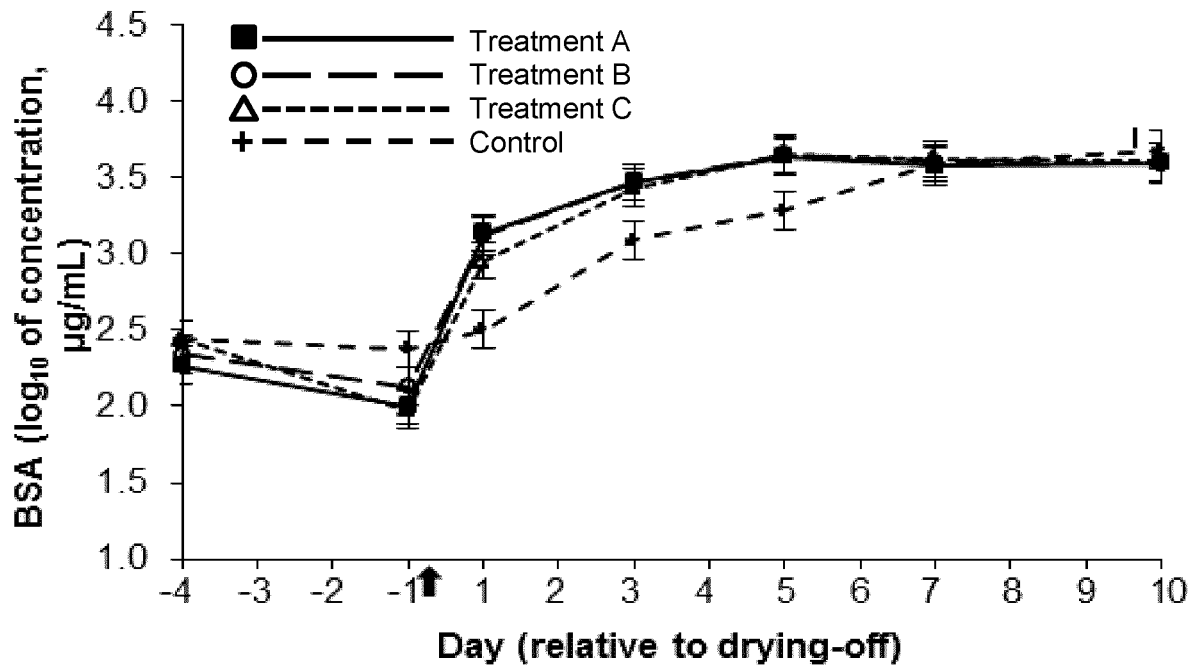
Figure 7D:
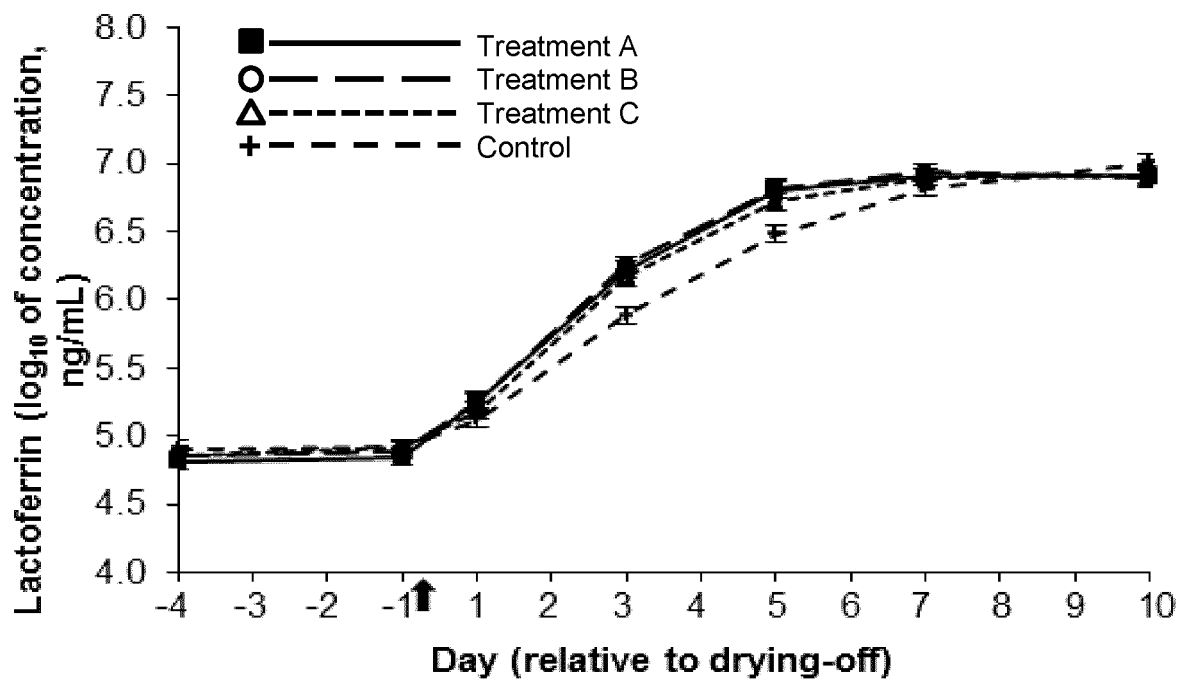
Figure 8A:
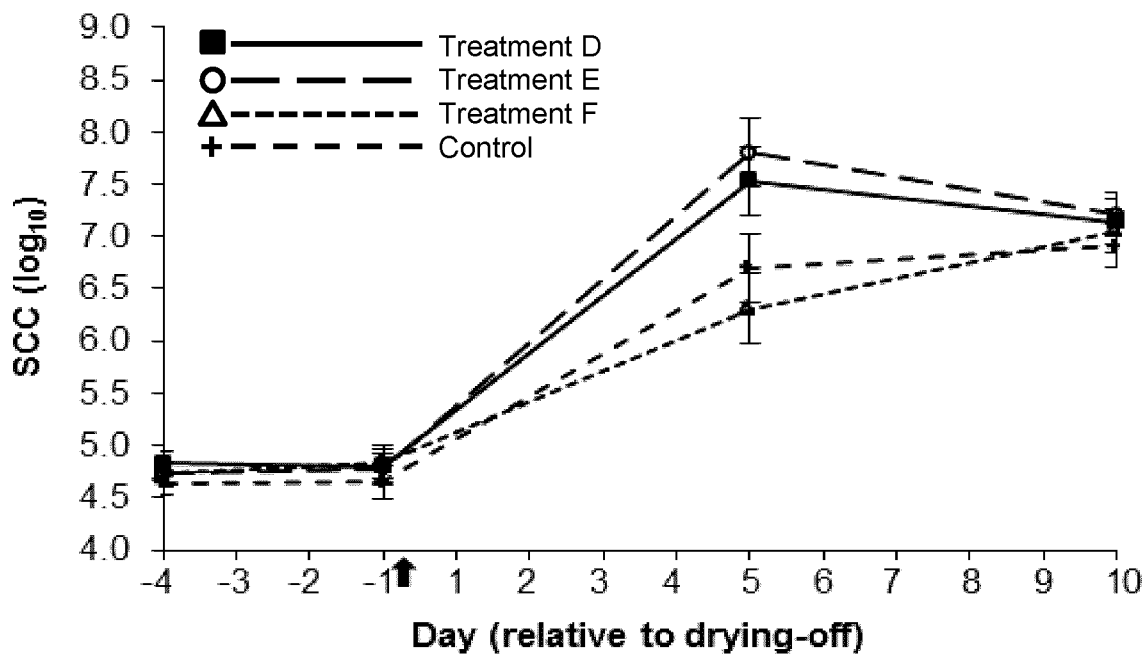
Figure 8B:
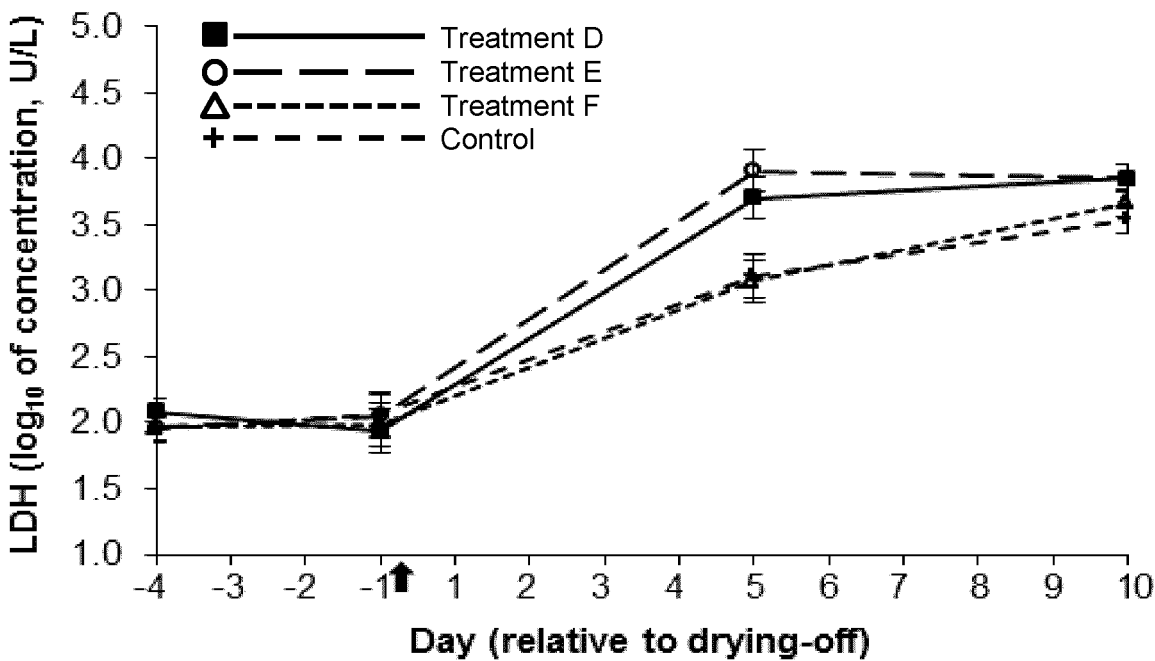
Figure 8C:
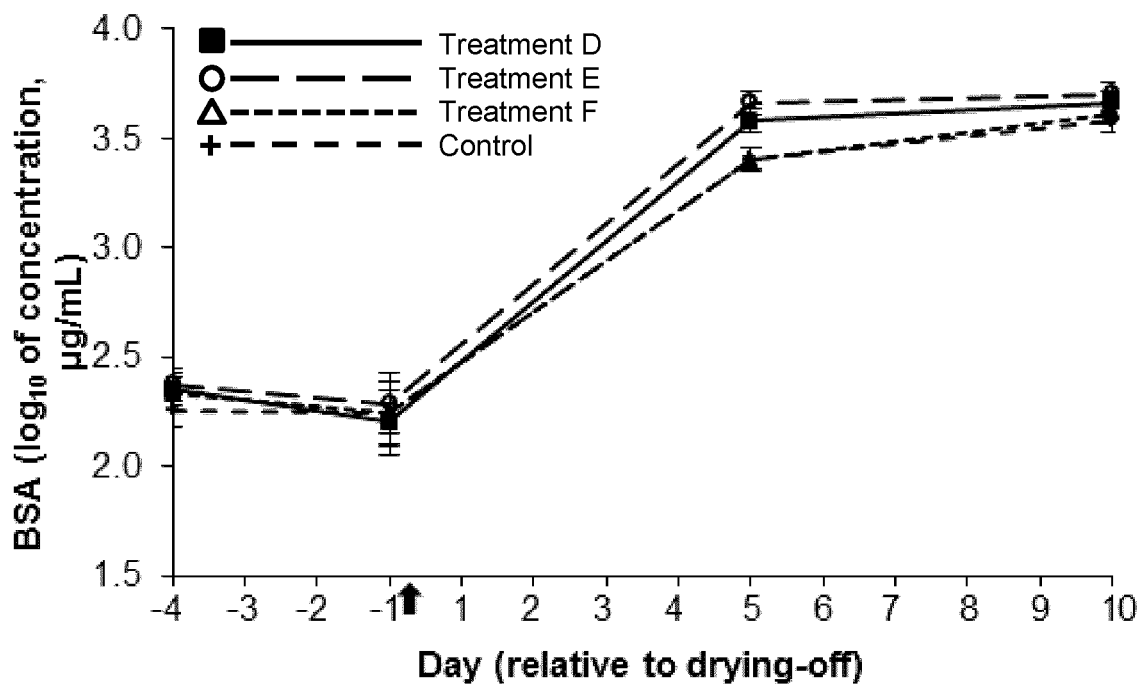
Figure 8D:
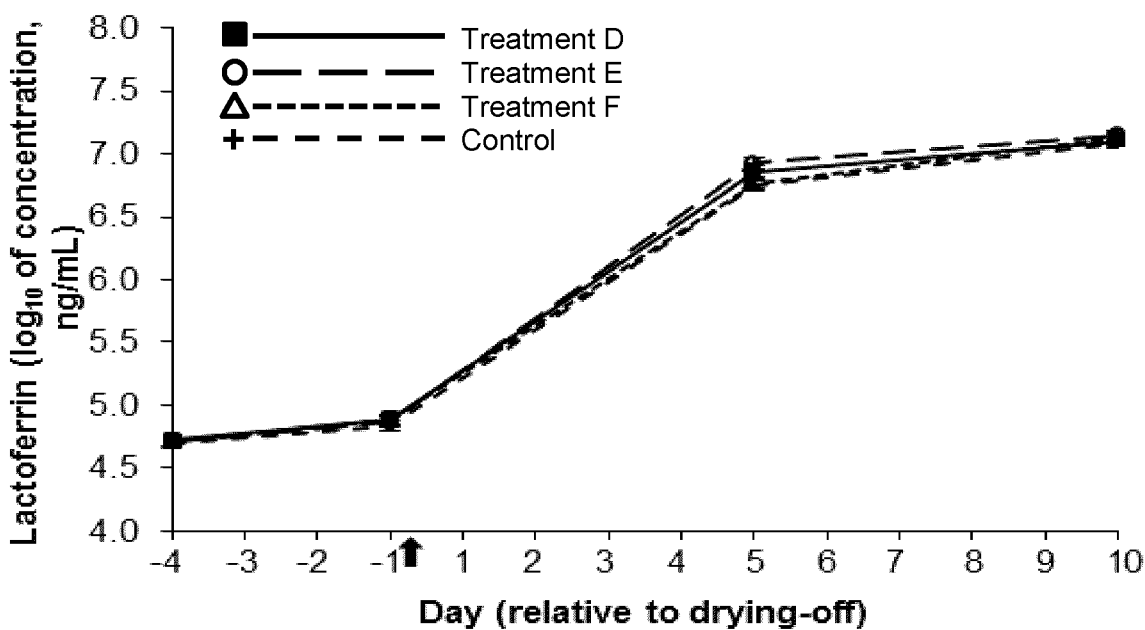

(right y axis) for a formulation of a medium molecular weight chitosan (chitosan B) and β-glycerophosphate at a concentration of 1.5% (w/v) mixed with water (panel a), pasteurized whole milk (panel b) or ultrafiltered whole milk (panel c) at 37° C.;

FIG. 7A is a graph showing the change in somatic cell count (SCC) over time in milk and mammary secretions from dairy cow udder quarters infused at drying-off with 5 mL of a 5% (w/v) hydrogel formulation of low-viscosity medium molecular weight chitosan (chitosan B) (Treatment A; n=7), 2.5 mL of a 5% (w/v) hydrogel formulation of low-viscosity chitosan B (Treatment B; n=7), 5 mL of a 5% (w/v) hydrogel formulation of high-viscosity chitosan B (Treatment C; n=7), or water (control; n=7). Treatment time is indicated by an arrow. Data are presented as least squares means±standard error of the means of $\log_{10}$-transformed values;

FIG. 7B is a graph showing the change in lactate dehydrogenase (LDH) activity over time in the milk and mammary secretions of FIG. 7A;

FIG. 7C is a graph showing the change in bovine serum albumin (BSA) concentration over time in the milk and mammary secretions of FIG. 7A;

FIG. 7D is a graph showing the change in lactoferrin concentration over time in the milk and mammary secretions of FIG. 7A;

FIG. 8A is a graph showing the change in somatic cell count (SCC) over time in milk and mammary secretions from dairy cow udder quarters infused at drying-off with 5 mL of a 2% (w/v) hydrogel formulation of low-viscosity medium molecular weight chitosan (chitosan B) (Treatment D; n=8), 4 g of teat sealant solution followed by 5 mL of a 2% (w/v) hydrogel formulation of low-viscosity chitosan B (Treatment E; n=8), 4 g of teat sealant solution (Treatment F; n=8), or water (control; n=8). Treatment time is indicated by an arrow. Data are presented as least squares means±standard error of the means of $\log_{10}$-transformed values;

FIG. 8B is a graph showing the change in lactate dehydrogenase (LDH) activity over time in the milk and mammary secretions of FIG. 8A;

FIG. 8C is a graph showing the change in bovine serum albumin (BSA) concentration over time in the milk and mammary secretions of FIG. 8A; and FIG. 8D is a graph showing the change in lactoferrin concentration over time in the milk and mammary secretions of FIG. 8A.

DETAILED DESCRIPTION

In at least one embodiment, the method of preventing intramammary infection includes administering a biological response modifier to one or more teats of a lactating mammal at drying-off. In at least one embodiment, the method comprises injecting the biological response modifier into the one or more teats of the lactating mammal. In at least one embodiment, the lactating mammal is a bovine. In at least one embodiment, the method further includes administration of an internal teat sealant. In at least one embodiment, the internal teat sealant is injected into the one or more teats before, concurrently with or after the injection of the biological response modifier.

Without being bound by theory, it is contemplated that the presence of a biological response modifier in the teat cistern could induce an inflow of immune cells into the teat. A sustained migration of fresh immune cells in the teat cistern during the early involution period is thought to aid in preventing the invasion of the mammary gland by pathogens. Use of an internal teat sealant along with administration of the biological response modifier could provide further protection against intramammary infection by helping to physically prevent bacteria from entering the teat.

In at least one embodiment, the biological response modifier will remain active within the teat during the active involution period, but will be biodegraded and eliminated from the teat prior to re-commencement of lactation. In at least one embodiment, the biological response modifier will be biodegraded within the teat within 3 weeks. In at least one embodiment, the biological response modifier can induce recruitment and moderate activation of somatic immune cells in the udder quarter while avoiding acute symptoms of inflammation of the mammary gland and/or or causing only minimal or moderate inflammation symptoms.

Thus, in at least one embodiment, the biological response modifier may show one or more of the following advantages:
  may induce at least a moderate recruitment of immune cells;
  may avoid acute inflammation and/or cause only moderate or minimal inflammation;
  may cause effects which are limited to the quarter which is infused with the biological response modifier;
  may produce immunostimulation for most or all of the period of active involution;
  may remain in contact with the interior tissues of the teat even if milk leakage occurs in the days following drying-off;
  may be biodegraded and eliminated from the teat prior to commencement of lactation; and
  may be used in combination with an internal teat sealant.

In at least one embodiment, the biological response modifier contains a chitosan hydrogel formulation. In at least one embodiment, the chitosan hydrogel formulation is formed by neutralizing an acidic solution of chitosan with a weak base. In at least one embodiment, the acidic solution of chitosan has a pH value of about 3 prior to neutralization with the weak base. In at least one embodiment, the weak base has a $pK_a$ value of about 6 to about 7. In at least one embodiment, the weak base has a $pK_a$ value of about 6.5. In at least one embodiment, the weak base is a β-glycerophosphate salt. In at least one embodiment, the chitosan hydrogel formulation is formed by adding the β-glycerophosphate salt to the acidic solution of chitosan until the pH of the resulting mixture is about 6.8. In at least one embodiment, the ρ-glycerophosphate salt is β-glycerophosphate disodium salt.

Without being bound by theory, it is considered that the use of a weak base having a $pK_a$ value close to the $pK_a$ of chitosan (which is about 6.5) to neutralize the acidic solution of chitosan will allow the chitosan to remain soluble at temperatures at or below room temperature (about 25° C.) but to form a hydrogel upon heating, for example, to a temperature close to the body temperature of a mammal, or to a temperature of about 37° C. to about 39° C.

In at least one embodiment, the chitosan has a degree of deacetylation of at least 90%. In at least one embodiment, the chitosan has a weight average molecular weight of from about 110 kD to about 250 kD. In at least one embodiment, the chitosan has a weight average molecular weight of from about 150 kD to about 175 kD. In at least one embodiment, the chitosan has a weight average molecular weight of from about 160 kD to about 170 kD. In at least one embodiment, the chitosan has a viscosity from about 90 cP to about 130 cP, when measured for a 1% solution of the chitosan in 1% acetic acid at 20° C. In at least one embodiment, the chitosan is soluble at acidic pH. In at least one embodiment, the chitosan is soluble at a pH of about 3.

In at least one embodiment, the chitosan hydrogel formulation can remain liquid at refrigerator temperature (from about 0° C. to about 4° C.). In at least one embodiment, the chitosan hydrogel formulation can remain liquid for more than an hour at room temperature (about 25° C.). In at least one embodiment, the chitosan hydrogel formulation will have an extrusion force of about 400 g to about 800 g at a temperature of about 22° C. In at least one embodiment, the chitosan hydrogel formulation will form a gel at body temperature (about 37° C. to about 39° C.). In at least one embodiment, the chitosan hydrogel formulation can form a gel at a temperature of about 37° C. to about 39° C. within about 30 minutes, or within about 15 minutes, or within about 10 minutes, or within about 5 minutes, or within about 4 minutes, or within about 3 minutes, or within about 2 minutes, or within about 1 minute.

Advantageously, the chitosan hydrogel remains fluid at room temperature for a sufficient amount of time to permit convenient injection into a teat, but once the chitosan hydrogel is injected into the teat and reaches body temperature (approximately 37° C. to approximately 39° C.), a gel is promptly formed, allowing the chitosan hydrogel to remain within the teat with minimal leakage, and in close contact with the internal tissue of the teat, including but not limited to the Furstenberg's rosette.

In at least one embodiment, the chitosan hydrogel undergoes biodegradation within a teat of a lactating mammal. In at least one embodiment, the chitosan hydrogel can be biodegraded by enzymes present in milk, including but not limited to one or more of lysozymes, N-acetyl-D-glucosaminidases and lipases. In at least one embodiment, the chitosan hydrogel can be biodegraded and eliminated from the teat prior to re-commencement of lactation. In at least one embodiment, the chitosan hydrogel can be biodegraded within the teat within 3 weeks after injection into the teat.

Definitions

As used herein, the term "udder" is intended to refer to the organ which contains the milk-producing mammary glands of a four-legged mammal, including but not limited to cattle, sheep, goats, deer and other ruminants. As used herein, the term "quarter" is intended to refer to one of the four mammary glands in a bovine udder. As used herein, the term "teat" is intended to refer to the protuberance through which milk is released from a mammary gland.

As used herein, the term "mammary secretions" is intended to refer to the secretions produced by the mammary gland, including but not limited to milk during the period of lactation and other secretions, which may or may not contain some milk, which are produced by the mammary gland during drying-off and/or dry periods. Mammary secretions may remain inside the mammary gland and/or be released through the teat.

As used herein, the terms "liquid" and "fluid" as used herein when referring to a composition of a present biological response modifier as described herein are intended to mean that the composition is suitable for facile manual injection into a teat using a suitably sized syringe, as understood by a person skilled in the art.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, an object that is "substantially" aligned would mean that the object is either completely aligned or nearly completely aligned. The exact allowable degree of deviation from absolute completeness may, in some cases, depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

EXAMPLES

Other features of the present invention will become apparent from the following non-limiting examples which illustrate, by way of example, the principles of the invention.

Example 1: Preparation of Chitosan Hydrogel Formulations

From an initial screen of chitosan samples of varying molecular weights and degrees of deacetylation, three chitosan types were selected for further testing:

Chitosan A (low molecular weight or food grade chitosan; molecular weight 110 kDa, 92.5% deacetylation, G.T.C. Union Group-Bio Corp. Qingdao, China);

Chitosan B (medium molecular weight or acid soluble chitosan; molecular weight 166.7 kDa, 91.6% deacetylation, Qingdao Yuda Century Economy And Trade Co., Ltd., Qingdao, China); and Chitosan C (high molecular weight or high density chitosan; molecular weight 250 kDa, 95.6% deacetylation, G.T.C. Union Group-Bio Corp. Qingdao, China).

Hydrogel formulations of each chitosan type (A, B and C) at concentrations (weight/volume) of 0.5%, 1% and 1.5% were prepared by adding chitosan to 80 mL of water and adjusting the pH of the mixture to about 3 by addition of 6.00 N HCl. The mixture was allowed to stand at room temperature overnight, the pH was adjusted to about 6.8 by addition of a 50% (w/v) aqueous solution of β-glycerophosphate and the final volume of the solution was adjusted to 100 mL by addition of water.

Example 2: Rheological Properties of Chitosan Hydrogels

Figure 1A:
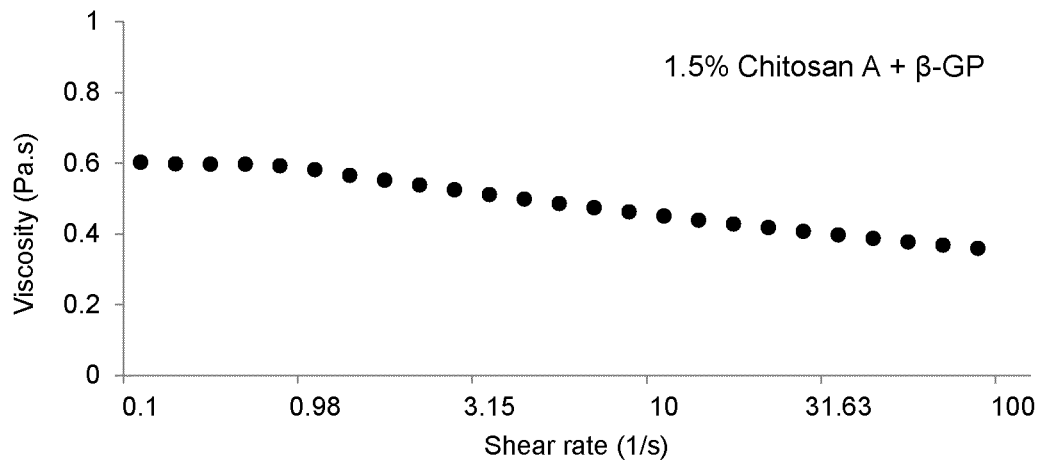
FIG. 1A is a graph showing the shear dependent viscosity of a formulation of a low molecular weight chitosan (chitosan A) and β-glycerophosphate at a concentration of 1.5% (w/v)
Figure 1B:
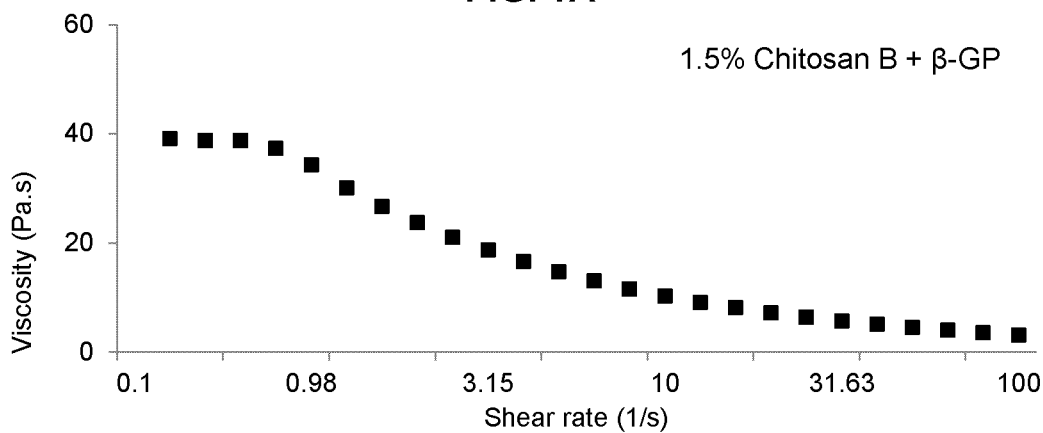
FIG. 1B is a graph showing the shear dependent viscosity of a formulation of a medium molecular weight chitosan (chitosan B) and β-glycerophosphate at a concentration of 1.5% (w/v)
Figure 1C:
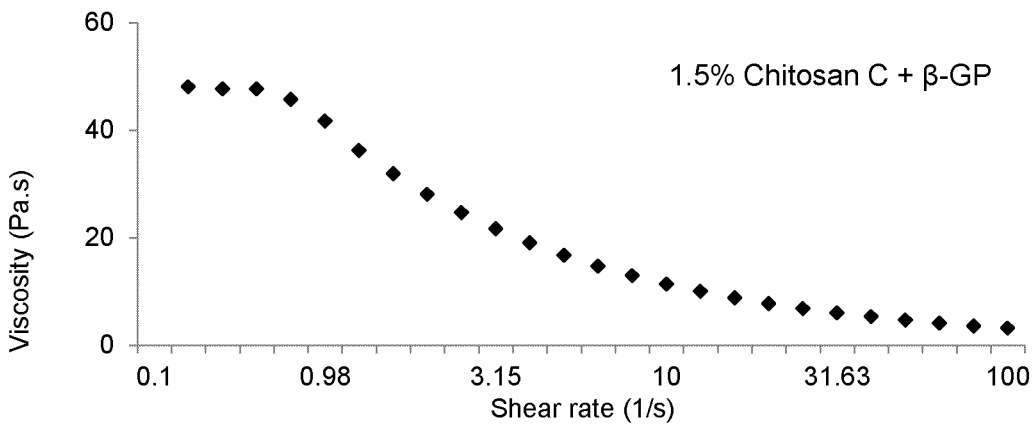
FIG. 1C is a graph showing the shear dependent viscosity of a formulation of a high molecular weight chitosan (chitosan C) and β-glycerophosphate at a concentration of 1.5% (w/v)

Flow behavior index (n), consistency coefficient (m), and apparent shear viscosity ($\eta_v$) as a function of shear rate in the range of 0.1/s to 100/s at 22° C. of bulk media containing hydrogel formulations of chitosan prepared as described in Example 1 were measured using an AR1000 Rheometer (TA Instrument, New Castle, Del., U.S.A.). Plots of viscosity vs. shear rate for formulations containing 1.5% w/v of chitosans A, B and C are shown in FIGS. 1A-C.

Dynamic properties including storage modulus (G'), loss modulus (G") and delta degree $$\left(\delta^\circ; i\frac{G''}{G'}\right),$$

of the formulations were evaluated using an AR1000 Rheometer (TA Instrument, New Castle, Del., U.S.A.) as a function of frequency (1-25 rad/s) at constant temperature (room temperature) by first increasing stress from 0.01 Pa-100 Pa at a constant frequency of 1 Hz followed by increasing frequency at 1-100 rad/sec at constant stress of 1 Pa to assure applied stress and frequency are in the linear region. The elastic retention was expressed as apparent delta degree $$\left(i\frac{G''}{G'}\right)$$

and compared at elevated applied frequency (25 rad/s). The results are shown in Table 1:

TABLE 1

| | Power law rheological parameters (mean ± standard deviation) for chitosan formulations. | | | | | |
|---|---|---|---|---|---|---|
| Formulation[1] | n | M(Pa) | $\eta_o$ (Pa · s) | G'(Pa) | G"(Pa) | δ° (°) |
| A 0.5% | 0.92 ± 0.01 | 0.37 ± 0.01 | 0.27 ± 0.01 | 2.45 ± 0.20 | 6.13 ± 0.22 | 75.12 ± 1.32 |
| 1% | 0.89 ± 0.10 | 0.58 ± 0.01 | 0.43 ± 0.00 | 3.79 ± 0.12 | 8.94 ± 0.24 | 67.05 ± 0.08 |
| 1.5% | 0.75 ± 0.01 | 3.11 ± 0.02 | 1.15 ± 0.03 | 5.29 ± 0.13 | 11.58 ± 0.22 | 63.50 ± 1.44 |

TABLE 1-continued

Power law rheological parameters (mean ± standard deviation) for chitosan formulations.

| Formulation[1] | | n | M(Pa) | $\eta_o$ (Pa · s) | G'(Pa) | G"(Pa) | δ° (°) |
|---|---|---|---|---|---|---|---|
| B | 0.5% | 0.51 ± 0.00 | 24.50 ± 0.10 | 0.43 ± 0.00 | 3.24 ± 0.04 | 0.88 ± 0.01 | 19.82 ± 0.20 |
|   | 1%   | 0.48 ± 0.01 | 33.82 ± 0.17 | 1.15 ± 0.03 | 3.84 ± 0.06 | 0.92 ± 0.00 | 17.62 ± 0.05 |
|   | 1.5% | 0.45 ± 0.01 | 43.82 ± 0.19 | 2.15 ± 0.03 | 4.32 ± 0.08 | 1.05 ± 0.03 | 14.24 ± 0.38 |
| C | 0.5% | 0.49 ± 0.01 | 28.81 ± 0.01 | 1.34 ± 0.06 | 9.38 ± 0.59 | 8.52 ± 0.13 | 9.14 ± 0.34 |
|   | 1%   | 0.44 ± 0.01 | 41.15 ± 0.03 | 6.81 ± 0.05 | 112.25 ± 0.21 | 34.25 ± 0.27 | 8.46 ± 0.13 |
|   | 1.5% | 0.38 ± 0.00 | 57.52 ± 0.00 | 18.46 ± 0.00 | 138.46 ± 0.45 | 48.18 ± 0.05 | 7.67 ± 0.12 |

[1]A = chitosan A; B = chitosan B; C = chitosan C
n: Flow behavior index
m: Consistency coefficient
η°: Newtonian viscosity (0.1/s)
G': Storage (elastic) modulus
G": Loss (viscosity) modulus δ°: Delta degree $\left(i\frac{G''}{G'}\right)$ As seen in FIGS. 1A-C, all tested formulations having concentrations of 1.5% chitosan show constant viscosity at low shear rates (Newtonian viscosity, $\eta_o$ or viscosity at rest), and pseudoplastic, shear-thinning or power-law behavior at higher shear rates, where viscosity decreases with increasing shear rate. As seen in Table 1, the values of flow behaviour index (n) are less than unity for each formulation, further indicating that the chitosan formulations are shear-thinning. As the molecular weight of the chitosan in the formulation increases (chitosan A<chitosan B<chitosan C), viscosity becomes more dependent on shear rate, and the formulations become more pseudoplastic. Formulations which show higher pseudoplastic behaviour could possibly be pumped or injected more easily at higher shear. In addition, as the concentration of the chitosan in each formulation increases from 0.5% to 1.5% (w/v), flow behaviour index decreases and consistency coefficient (m), decreases, indicating that less concentrated mixtures flow more readily.

The delta degree(δ°) or phase shift angle is related to the proportion of loss modulus (G", a measure of viscous properties) over storage modulus (G', a measure of elastic properties). For purely viscous non-elastic systems, the value of δ° is 90° whereas for purely elastic systems, the value of δ° is 0°. Therefore, a value of δ° between 0° and 90° indicates the relative elasticity and viscosity of a system. Furthermore, when the values of G' and G" for a substance are changing as a function of frequency or some other parameter, the point at which G' and G" "cross over" each other represents a transition point between the liquid and gel phases. As seen in Table 1, for formulations including both chitosan B and chitosan C, storage (elastic) modulus G' is greater than loss (viscous) modulus G" (G'>G") and the resultant delta degree $$\left(i\frac{G''}{G'}\right)$$

is therefore less than 45' confirming that formation of a gel is possible. In contrast, the values for the formulation including chitosan A show that loss (viscous) modulus G" is higher than storage (elastic) modulus G' and the resultant delta degree $$\left(i\frac{G''}{G'}\right)$$

is therefore much higher than the gelling point of 45°.

Example 3: Extrusion Force and Energy

The force and energy required to displace chitosan hydrogel formulations prepared as described in Example 1 were determined, using a procedure similar to that reported by Leon et al. (2016), Journal of Food Engineering 188, 1-7. A 10 mL syringe of 84 mm length and interior diameter of 14 mm equipped with a plunger of 30 mm length and 13.5 mm diameter and with a nozzle with opening of 1 mm and length of 30 mm was adapted as an extrusion cell. For each formulation, 5 mL samples of each formulation having a height of 32 mm, prior to and after gelation, or 5 mL of distilled deionized (DDI) water as a control, were placed inside the syringe and extruded for 26 mm within 5 second using a texture analyzer (Texture Technology, New Jersey).

Figure 2:
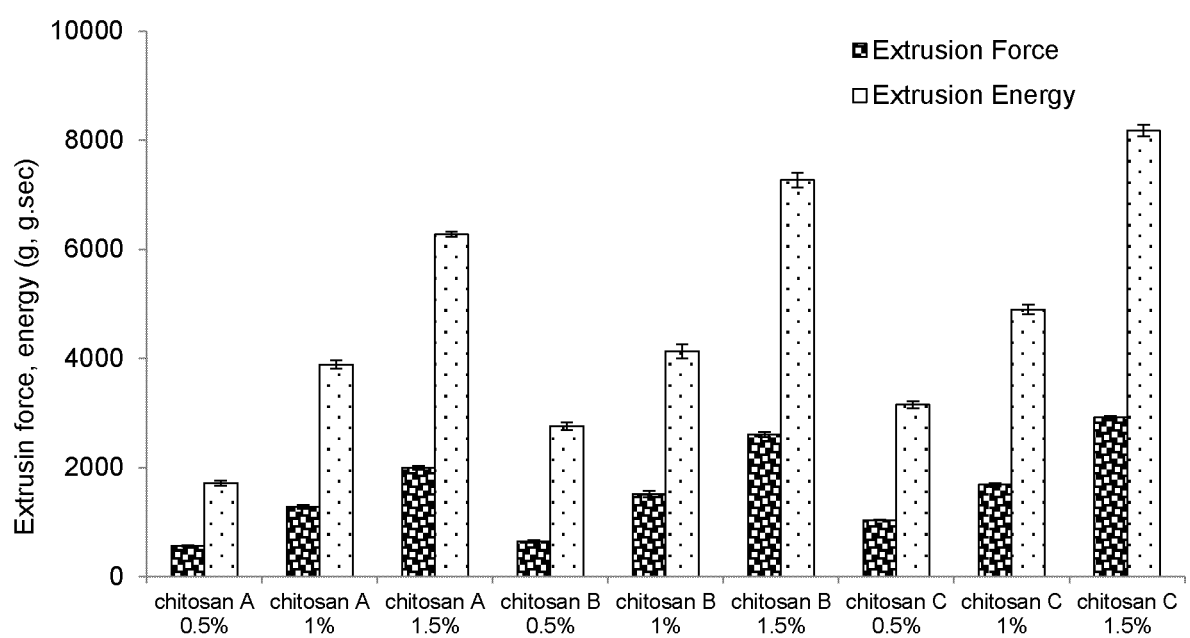
FIG. 2 is a bar graph showing extrusion force and extrusion energy of various formulations of low molecular weight chitosan (chitosan A), medium molecular weight chitosan (chitosan B) and high molecular weight chitosan (chitosan C) and β-glycerophosphate at concentrations (w/v) of 0.5%, 1% and 1.5%.

The force and energy needed to extrude the formulations are shown in FIG. 2. In general, both the extrusion force and the extrusion energy of all chitosan formulations were greater than those of water. In addition, the values of the extrusion force and the extrusion energy increased with both the concentration and the molecular weight of the chitosan (chitosan A having the lowest molecular weight and chitosan C having the highest molecular weight). These results are consistent with the observed increase in pseudoplasticity, as indicated by the increasing flow rate and consistency coefficient, as the molecular weight of the chitosan increases (Table 1).

Example 4: Heat-Induced Liquid-Gel Transition of Chitosan Hydrogels

Figure 3:
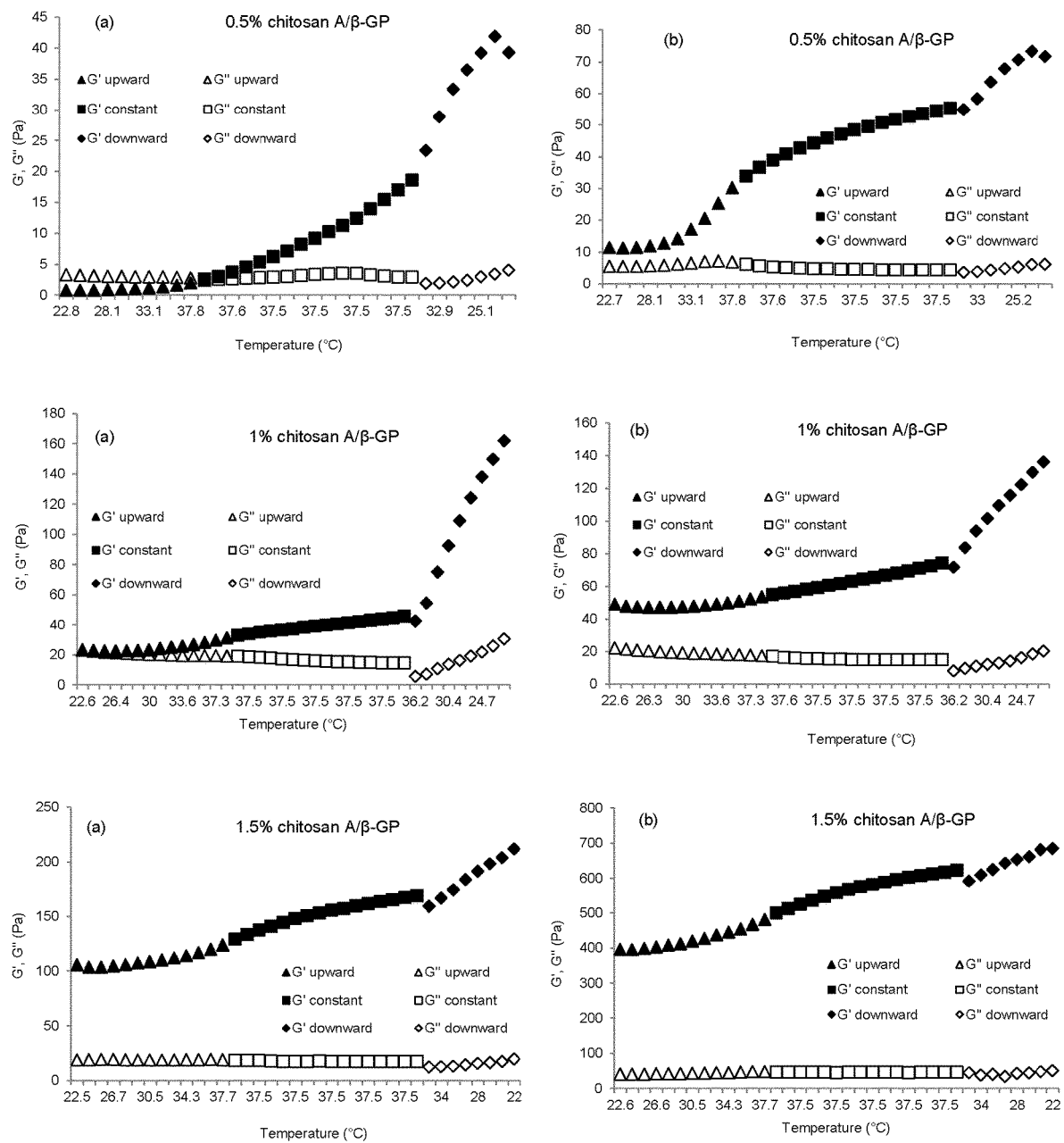
FIG. 3 is a series of graphs showing the change of storage (elastic) modulus (G') and loss (viscous) modulus (G") with temperature for formulations of a low molecular weight chitosan (chitosan A) and β-glycerophosphate at varying concentrations (0.5%, 1% and 1.5% (w/v)) immediately after preparation (panels a) and one hour after preparation (panels b). G' and G" upward refer to values of G' and G" when the temperature is increasing; G' and G" constant refer to values of G' and G" when the temperature is constant; and G' and G" downward refer to values of G' and G" when the temperature is decreasing.
Figure 4:
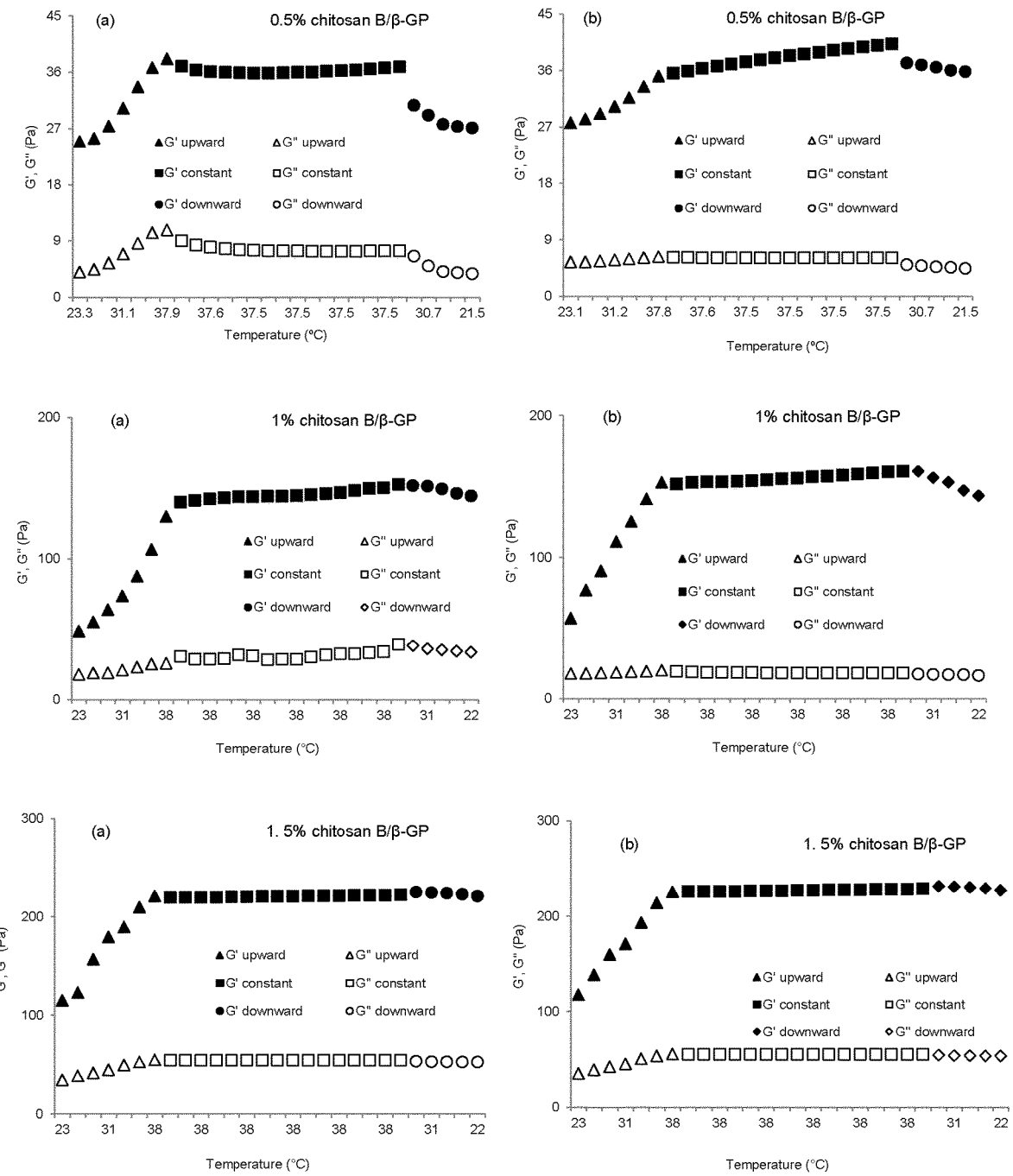
FIG. 4 is a series of graphs showing the change of storage (elastic) modulus (G') and loss (viscous) modulus (G") with temperature for formulations of a medium molecular weight chitosan (chitosan B) and β-glycerophosphate at varying concentrations (0.5%, 1% and 1.5% (w/v)) immediately after preparation (panels a) and one hour after preparation (panels b). G' and G" upward, G' and G" constant and G' and G" downward have the same meaning as for FIG. 3.
Figure 5:
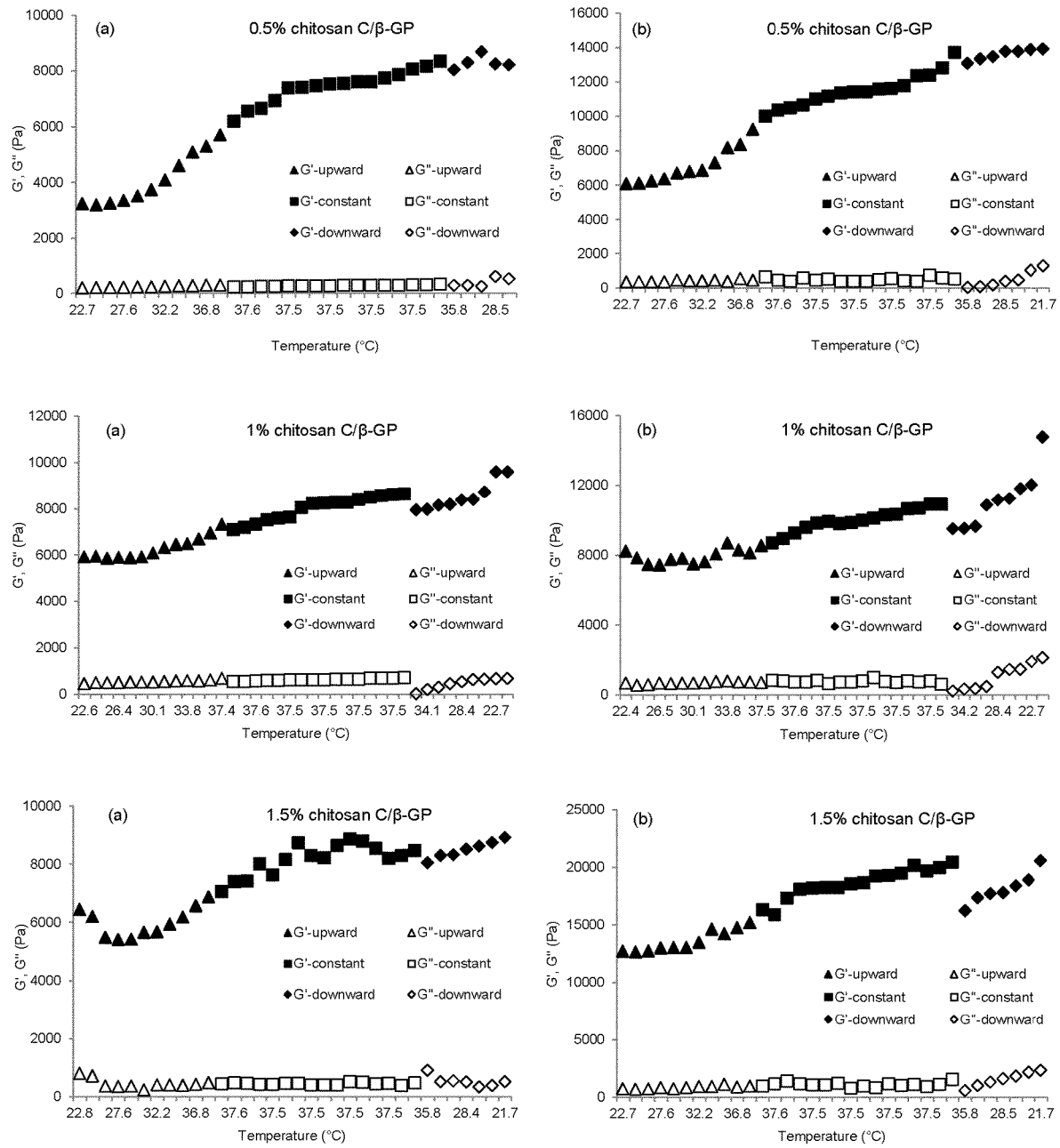
FIG. 5 is a series of graphs showing the change of storage (elastic) modulus (G') and loss (viscous) modulus (G") with temperature for formulations of a high molecular weight chitosan (chitosan C) and β-glycerophosphate at varying concentrations (0.5%, 1% and 1.5% (w/v)) immediately after preparation (panels a) and one hour after preparation (panels b). G' and G" upward, G' and G" constant and G' and G" downward have the same meaning as for FIG. 3.

The heat induced phase transition (liquid to gel) of chitosan hydrogel formulations prepared as described in Example 1 was measured via dynamic rheometry by determining the temperature at which G' and G" "cross over" each other. Temperature development of G' and G" were evaluated while heating from 22° C. up to 37.5° C., keeping at constant temperature of 37.5° C. for 3 min and cooling from 37.5° C. down to 22° C. The time taken to reach the desired temperatures was calibrated by placing 5 ml of each chitosan hydrogel formulation prepared as described in Example 1 into a dialysis bag and inserting a thermocouple in the center point of the bag. The dialysis bag was then immersed in the water-bath and the time required for the temperature of the solution in the dialysis bag to increase from 22° C. to 37.5° C. was recorded. Experiments were conducted on formulations prepared according to Example 1 immediately after preparation and after standing at room temperature for one hour. Stress was kept constant at 1 Pa and frequency was kept constant at 1 Hz during the measurement. The results are shown in FIGS. 3, 4 and 5. In each of FIGS. 3 to 5, panels a) show measurements made immediately after preparation of each formulation, while panels b) show measurements made after the formulation had been kept at room temperature for 1 hour.

As seen in FIGS. 3 to 5, gel strength, as indicated by the storage (elastic) modulus G', increases with increasing temperature, and with increasing concentration and molecular weight of the chitosan in the formulation. In addition, for formulations of chitosans A and C, significant increases in gel strength could be seen after the formulations were kept at room temperature for one hour. In contrast, the gel strength of formulations of chitosan B remained relatively constant even after standing at room temperature for one hour. Thus, formulations of chitosan B show more predictable and consistent gelling behaviour, and were selected for further testing.

Example 5: Stability of Chitosan Hydrogel Formulations Exposed to Water and Milk Individual 5 mL portions of a hydrogel formulation containing 1.5% (w/v) of chitosan B prepared as described in Example 1 were each added to 5 mL of water, pasteurized whole milk, or ultrafiltered whole milk at 37° C. and at a pH of about 6.5. The mixtures were stored at 37° C. for up to seven days (start of storage is day 0). Samples of each mixture (n=3) were collected on each of days 1 to 7, filtered through a pre-weighed funnel screen and allowed to drain for 60 minutes to separate the gel from the liquid media. The screen containing the drained gel was weighed and the weight of the gel was calculated using the formula:

Weight of gel=weight of screen containing the gel–weight of screen

In addition, loss of elasticity of stirred samples of the mixture of the hydrogel formulation and medium (water or milk) was determined in duplicate daily during the storage period by measuring delta degree $$\left(i\frac{G''}{G'}\right)$$

as described in Example 2. The results are shown in FIG. 6.

Figure 6:
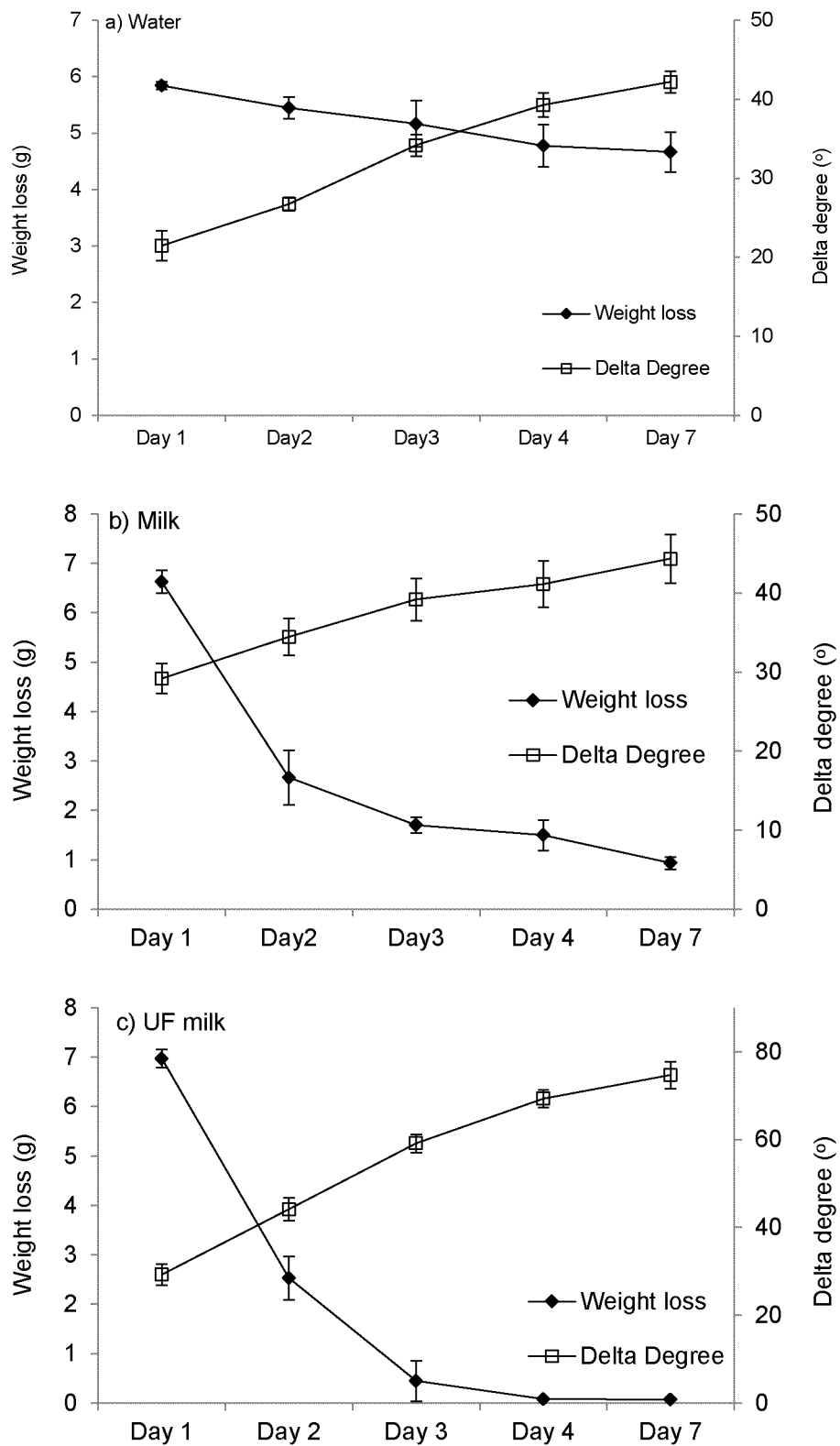
FIG. 6 is a series of graphs comparing weight loss (left y axis) and loss of elasticity as indicated by delta degree $$\left(\delta^\circ; i\frac{G''}{G'}\right)$$

As seen in FIG. 6, the chitosan hydrogel samples exposed to milk showed a greater increase in weight on day 1 and a more rapid loss in weight over the following days than did the samples exposed to water. It is thought that the chitosan may have reacted with the casein proteins in milk to form coagulated casein micelles, which initially added to the weight of the drained gel. However, as the exposure to milk continued, the chitosan gel appeared to degrade and its weight decreased.

In addition, exposure to both water and milk resulted in a loss of elasticity, as evidenced by the increase in delta degree. Exposure to water for seven days at 37° C. resulted in an increase in delta degree from a value of 21.46° on day 1 to a value of 42.19° on day 7. However, the value still remains below 45°, indicating that a gel network was retained in the water medium. In the presence of pasteurized milk, a similar loss of elasticity was observed. However, in the presence of ultrafiltered milk, the chitosan formulation essentially lost its ability to form a gel after day 3 at 37° C., and by day 7, showed a delta degree value of 74.67°, indicating almost completely viscous behaviour and a high loss of elasticity. The results indicate that chitosan hydrogel formulations could undergo degradation within a cow teat within several days or a few days, and thus be cleared from the teat before commencement of a subsequent lactation.

Example 6: Bacteriostatic Properties of Chitosan Hydrogels

The bacteriostatic activity of the chitosan hydrogels against strains of *Staphylococcus aureus*, *Streptococcus uberis* and *Escherichia coli* is evaluated by monitoring change in turbidity (absorbance at 640 nm) of cell culture media containing the chitosan hydrogels over time.

Tests were performed to evaluate the effect of concentration and storage conditions (temperature and time) on the antimicrobial properties (bactericidal and/or bacteriostatic) of the chitosan hydrogel. The tests were done on 10 mL syringes containing 5 g of hydrogel formulations prepared as described in Example 1. Half contained a hydrogel at a concentration of 1.5% chitosan and the other half at a concentration of 2.0% chitosan. For each concentration, one half was stored at 4° C. and the other half at 22° C. The syringes were stored for 1 h, 48 h or 168 h for each concentration and temperature. After storage, the hydrogel was applied on trypticase soy agar pre-inoculated with 200 µL of infected milk, then incubated at 37° C. for 48 h. After incubation, the plates were observed. For all treatments, no bacterial growth was observed at the precise location where the hydrogel was applied in comparison with the rest of the agar where there was the presence of colonies.

Example 7: Intramammary Infusion of Chitosan Hydrogels in Cows in Late Lactation Statistical Analysis Data were analyzed by ANOVA using the MIXED procedure of SAS™ software version 9.0 (SAS Institute Inc., Cary, N.C.). Time was used as a repeated effect, and treatment (cow) was used as the subject. For inflammation score, orthogonal contrasts were performed to compare the effect of each treatment to that of the control. For other parameters, the following contrasts were used: treatments A+B+C vs. control; treatments A+B vs. treatment C; and treatment A vs. treatment B. Other treatment comparisons were performed using the Tukey-Kramer adjustment. When variances were not homogeneous, data were $\log_{10}$-transformed prior to analyses. Differences were considered statistically significant when P 0.05 and considered a trend when P<0.1.

Preparation of Chitosan Hydrogel Treatments

All treatments were prepared with aseptic, nonpyrogenic products and materials under a laminar flow hood. Acid-soluble chitosan (Chitosan B as described in Example 1 above; molecular weight 166.7 kDa, 91.6% deacetylation) of high-viscosity (130-centipoise) or low-viscosity (90-centipoise) was provided by Qingdao Yuda Century Economy and Trade Co. (Shibei District, Qingdao, China). For each concentration of chitosan (2% and 5% (w/v)), a 200-mL solution was made by adding 120 mL of nonpyrogenic water (<0.005 endotoxin units/mL; Lonza, Walkersville, Md.) to preweighed chitosan. The solution was agitated at 200 rpm with a metal mixing rod. The pH of the solution was reduced to 3 via the addition of 0.1 M HCl (Sigma-Aldrich Co., St. Louis, Mo.). The preparation was kept overnight at room temperature for complete hydration. The following day, the pH of the preparation was adjusted to 6.8 using a 50% (w/v) solution of β-glycerophosphate disodium salt hydrate (Sigma-Aldrich Co.). Then, the volume was adjusted to 200 mL by the addition of nonpyrogenic water (Lonza) to form hydrogel formulations. Plastic syringes were filled with the desired volume, sealed with a cap, and stored at room temperature.

Treatment of Animals and Sample Collection

Seven Holstein cows in late lactation (319±29 days in milk (DIM) at drying-off) producing more than 15 kg (average 22.6±1.9 kg) of milk per day were used. Cows were milked twice a day and projected or real 305 days milk production was 9312±749 kg. The group of cows was dried off at the same time, 90±17 days before expected calving date. Prior to dry-off (d −4), quarter somatic cell count (SCC) averaged 122,693±34,520 cell/mL. Before drying-off, the cows were fed ad libitum a late-lactation diet. After drying-off, the cows were fed ad libitum a dry period diet and dry hay. Water was available ad libitum during the whole experiment.

At drying-off, each udder quarter was randomly assigned to 1 of 4 intramammary infusions, as follows: 5 mL of a 5% (w/v) hydrogel formulation of low-viscosity chitosan (Treatment A; n=7), 2.5 mL of a 5% (w/v) hydrogel formulation of low-viscosity chitosan (Treatment B; n=7), 5 mL of a 5% (w/v) hydrogel formulation of high-viscosity chitosan (Treatment C; n=7), or nonpyrogenic water (Lonza) (control; n=7). Before the infusions, the teats were compressed at the top to keep the infused preparation in the teat.

Milk samples (200 mL) were manually collected from each quarter just before the morning milking on d −4 relative to drying-off as well as just before the last milking before drying-off (d −1). Mammary secretions from each quarter (100 mL) were manually collected aseptically on d 1, 3, 5, 7, and 10 after the last milking.

Inflammatory Response

Quarters were assessed for inflammation symptoms every 2 h for the first 12 h after the infusions and then 3 times per day (0900, 1300, and 1900 h) for the following 7 d. Inflammation was scored from 1 to 6 according to the mammary gland chart created by Rambeaud et al. (2003) Vet. Immunol. Immunopathol. 96:193-205, as follows: 1=normal; 2=slight swelling; 3=moderate swelling; 4=severe swelling; 5=scar tissue; and 6=edema. Rectal temperature was determined at the same time.

The udder quarter inflammation scores for the periods from 0 to 24 h, 25 to 48 h, and 49 to 170 h after the infusions are presented in Table 2. Data are presented as least squares means.

TABLE 2

| | Average inflammation scores | | | | | | | |
|---|---|---|---|---|---|---|---|---|
| | Treatment | | | | | P-value | | |
| | | | | | | A vs. | B vs. | C vs. |
| Period | A | B | C | CTRL | SEM[1] | CTRL | CTRL | CTRL |
| 0-24 h | 1.39 | 1.39 | 1.13 | 1.02 | 0.07 | <0.01 | <0.01 | 0.31 |
| 25-48 h | 1.09 | 1.28 | 1.11 | 1.24 | 0.05 | 0.06 | 0.63 | 0.09 |
| 49-170 h | 1.11 | 1.11 | 1.05 | 1.16 | 0.06 | 0.51 | 0.52 | 0.21 |

[1]SEM = Standard Error of the Mean

In the period from 0 to 24 h, the average inflammation scores were slightly greater in the quarters treated with Treatments A (P<0.01) and B (P<0.01) than in the control quarters. Conversely, the quarters treated with Treatment C were not significantly (P>0.1) different from the control quarters in terms of inflammation scores. No differences in inflammation scores were observed after 24 h (P>0.1). The results show that treatment with chitosan is associated with only early mild and transient symptoms of inflammation if any, and does not cause acute inflammation of the mammary gland.

Bacterial Concentration

Milk and mammary secretion samples were plated just after collection on tryptic soy agar, mannitol salt agar, and MacConkey II agar (Becton, Dickinson and Company, Mississauga, ON, Canada). The plates were then incubated at 37° C. for 24 h before colonies were counted. Cow udder quarters infected with pathogens were excluded from the experiment. Accordingly, one quarter treated with Treatment B showed a bacterial infection on d 5, 7 and 10, and therefore data from this quarter on these days were omitted from further analysis.

Somatic Cell Counts

During early involution, the number of somatic cells increases, and the increased number of immune cells are important for mammary gland defense. At the Furstenberg's rosette, located at the internal end of the streak canal, immune cells enter the teat cistern to intercept invading bacteria before they reach the mammary gland. Thus, a treatment which increases somatic cell count (SCC) during the drying-off period would be expected to improve the defense of the mammary gland against invading pathogens. Quarters showing a bacterial infection were excluded from analysis so that bacterial infection could be eliminated as a cause of an increase in SCC.

Somatic cell counts (SCC) are determined from fresh whole milk samples and mammary secretion samples using an automatic cell counter (DeLaval International AB, Tumba, Sweden). Samples of mammary secretions were diluted with commercial microfiltered skim milk until the somatic cell count obtained was between 100 and 200 cells/μL.

The results are shown in FIG. 7A. No differences were observed between the quarters during the pretreatment period (on d −4 and −1) (P>0.1). Somatic cell count increased from the day of drying-off (d −1) to d 10 (P<0.001), regardless of the treatment. However, somatic cell count was greater (P<0.001) on d 1 to 5 in all the chitosan-treated quarters than in the control quarters. Except on d 1, when the SCC in the quarters treated with Treatments A and B was greater in comparison with that of the quarters treated with Treatment C (P<0.01), there were no differences between the chitosan-treated quarters. Thus, chitosan treatment is associated with a faster increase of immune cell release at drying-off.

Markers of Mammary Involution

As milk production decreases, the permeability of tight junctions between epithelial cells increases, allowing paracellular transport between the interstitial space and milk or mammary secretions. This transport can be assessed by measuring concentrations of serum albumin and immunoglobulin in the milk or mammary secretions.

As well, as the mammary secretory tissue regresses, changes in the composition of milk secretions occur. For example, epithelial cells produce more lactoferrin as involution progresses. Lactoferrin acts as an immune factor that protects the mammary gland, at least in part by disrupting the outer membrane of gram-negative bacteria and binding iron so that it is unavailable for iron-dependent bacteria.

In addition, the release of leukocytes into mammary secretions can be indicated by measuring lactate dehydrogenase (LDH) activity, as leukocytes have a high LDH activity. Increased LDH activity is also associated with damage to mammary epithelial cells.

Thus, measuring lactate-dehydrogenase activity and the concentration of bovine serum albumin and lactoferrin in milk and mammary secretions can provide an indication of the progress of mammary gland involution and immune cell release.

Skim milk and somatic cells were separated from milk and mammary secretion samples by centrifugation (1,000× g, 4° C., 20 min). Skim milk aliquots were stored at −20° C. prior to determination of lactate dehydrogenase (LDH) activity, bovine serum albumin (BSA) concentration and lactoferrin concentration.

The LDH assay was performed using the CytoTox 96 Non-Radioactive Cytotoxicity Assay kit (Promega, Madison, Wis.) according to the manufacturer's instructions. The intra- and interassay coefficients of variation were 1.8% and 3.5%, respectively.

The results are shown in FIG. 7B. No differences were observed between the quarters during the pretreatment period (on d −4 and −1) (P>0.1). LDH activity increased from the day of drying-off (d −1) to d 10 (P<0.001), regardless of the treatment. On d 1 to 7, LDH activity was greater in the quarters treated with chitosan (P<0.01) than in the control quarters, but there were no differences between the chitosan-treated quarters.

The concentration of BSA in milk and mammary secretion samples was evaluated by a colorimetric assay as previously described by Bouchard et al. (1999), J. Dairy Sci. 82:2574-2581, with some modifications. Briefly, 200 µL of a skimmed milk sample was mixed with 450 µL of water and 450 µL of a solution containing 1 volume of 1.2 mM bromocresol green dissolved in 5 mM NaOH, 3 volumes of 0.2 M succinic acid (pH 4.0), and 0.8% Brij-35 detergent. The sample was then mixed by inversion and centrifuged at room temperature (1,900×g, 10 min). The optical density of the supernatant was read at 640 nm using a SpectraMax™ 250 microplate reader (Molecular Devices, Sunnydale, Calif.). The intra- and interassay coefficients of variation were 4.6% and 7.6%, respectively.

The results are shown in FIG. 7C. No differences were observed between the quarters during the pretreatment period (on d −4 and −1) (P>0.1). BSA concentration increased from the day of drying-off (d −1) to d 10 (P<0.001), regardless of the treatment. The concentration of BSA was greater (P<0.001) on d 1 to 5 in the quarters treated with chitosan than in the control quarters, but there were no differences between the chitosan-treated quarters.

The concentration of lactoferrin in the skim milk and mammary secretions was measured by ELISA using a commercial bovine lactoferrin ELISA quantitation set (Bethyl Laboratories Inc., Montgomery, Tex.). The intra- and interassay coefficients of variation were 4.6 and 5.9%, respectively.

The results are shown in FIG. 7D. No differences were observed between the quarters during the pretreatment period (on d −4 and −1) (P>0.1). Lactoferrin concentration increased from the day of drying-off (d −1) to d 10 (P<0.001), regardless of the treatment. The lactoferrin concentration in all the chitosan-treated quarters was greater on d 3 (P<0.001) and 5 (P<0.01) in comparison with the control quarters, but there were no differences between the chitosan-treated quarters.

Identification of Somatic Cells by Flow Cytometry

Seven-color immunophenotyping of somatic cells was performed on samples collected on d −1 and 1. Milk samples (20 mL) were diluted with 20 mL of PBS 1× and centrifuged (1,000×g, 23° C., 15 min). The supernatant was removed, and the pellet was resuspended in 15 mL of washing buffer consisting of PBS 1×+1% BSA (Sigma-Aldrich Co.)+2% normal goat serum (Meridian Life Sciences, Memphis, Tenn.). The mixture was then centrifuged (500×g, 4° C., 10 min). Cell washing was repeated with 25 mL of washing buffer until no more fat could be observed. Washing buffer was added to the cell pellet to reach a concentration of approximately $1 \times 10^7$ somatic cells/mL. A control pool was made with 100 µL from each sample. A 100-µL volume from each sample and the pool were transferred into a 96-well round bottom plate. The plate was centrifuged (300×g, 4° C., 5 min), and the supernatant was removed. The cells were suspended with 100 µL of washing buffer containing the primary antibodies listed in Table 3.

TABLE 3

Antibodies used for somatic cell identification

| Targeted cells | Receptor/ marker | Secondary marker | Clone | Isotype | Secondary antibody | Fluorochrome[1] | Conc. (µg/mL) |
|---|---|---|---|---|---|---|---|
| Granulocytes | Pan-granulocyte[2] | | CH138A | IgM | | | 10 |
| | | | | | Rat anti-mouse-IgM[3] | PE/Cy7 | 0.2 |
| Monocytes/ macrophages | CD14[+][4] | | M5E2 | IgG2a | | PE/Cy5.5 | 15 |

TABLE 3-continued

Antibodies used for somatic cell identification

| Targeted cells | Receptor/marker | Secondary marker | Clone | Isotype | Secondary antibody | Fluorochrome[1] | Conc. (μg/mL) |
|---|---|---|---|---|---|---|---|
| T-lymphocytes | CD3[+2] | | MM1A | IgG1 | | | 10 |
| | | | | | Rat anti-mouse-IgG1[3] | rPE | 0.2 |
| T-lymphocytes (subpopulation) | CD3[+] | CD4[+5] | CC8 | IgG2a | | FITC | 7.5 |
| | | CD8[+5] | CC63 | IgG2a | | Alexa Fluor™ 647 | 3.75 |
| | | Gamma-delta[2] | GB21A | IgG2b | | | 5 |
| | | | | | Goat anti-mouse IgG2b[3] | APC/Cy7 | 0.5 |
| Non-T-lymphocytes (gamma-delta) | CD3[−], CD14[−] | Gamma-delta[2] | GB21A | | | | 5 |
| | | | | | Goat anti-mouse IgG2b[3] | APC/Cy7 | 0.5 |
| Non-T-lymphocytes (B-lymphocytes) | CD3[−], CD14[−] | B-cell receptor[6] | | | Goat anti-bovine IgG (H + L) | DyLight™ 405 | 3 |

[1] PE = phycoerythrin
Cy = cyanine
FITC = fluorescein isothiocyanate
APC = allophycocyanin
[2] Washington State University (WSU) Monoclonal Antibody Center, Pullman, WA
[3] SouthernBiotech, Birmingham, AL
[4] BioLegend, San Diego, CA
[5] AbD Serotec, Raleigh, NC
[6] Jackson ImmunoResearch, West Grove, PA The plate was incubated on ice in the dark for 25 min. The cells were then washed 3 times with washing buffer. The plate was centrifuged (300×g, 4° C., 3 min), and the cells were resuspended with 100 μL of washing buffer containing the secondary antibodies mix. The plate was incubated again on ice in the dark for 25 min, and the cells were washed 3 times. The cells were resuspended in 200 μL of washing buffer.

The samples were analyzed immediately on a BD FACSCanto™ II flow cytometer (BD Biosciences, Mississauga, ON, Canada) equipped with 3 lasers in a 4-2-2 configuration. The BD FACSDiva™ version 8.0.1 operating software (BD Biosciences) was used for data acquisition and data analysis. The proportion of each somatic cell type bearing the distinctive receptors found on granulocytes, monocytes, and lymphocytes (Table 3) was determined. Then, subclasses of T-lymphocytes and non-T-lymphocytes were assessed by using other specific receptors. During the design of the experiment, fluorescent probes were selected to minimize the amount of fluorescence compensation to be done inside the different types of cells analyzed. Before the beginning of the experiment, each primary antibody was titered and tested for cross-reactivity with secondary antibodies. None of the primary antibodies showed cross-reactions or unspecific binding of secondary antibodies. Finally, a single-stain marker and FMO (Fluorescence Minus One) cocktail were used to determine all gates.

The results are shown in Table 4. Data are presented as least squares means.

TABLE 4

Percentages of somatic cell types

| | Percentage of cells (%) Day −1 | | | | Percentage of cells (%) Day 1 | | | | | P-value | | |
|---|---|---|---|---|---|---|---|---|---|---|---|---|
| Cell type | A | B | C | CTRL | A | B | C | CTRL | SEM[1] | TRT[2] | Day | TRT*Day |
| Monocytes | 30.6 | 32.4 | 26.9 | 33.8 | 23.6 | 25.8 | 18.9 | 16.4 | 3.7 | 0.46 | <0.001 | 0.34 |
| Granulocytes | 45.6 | 44.3 | 52.7 | 43.9 | 62.4 | 50.2 | 60.6 | 67.0 | 6.3 | 0.50 | <0.001 | 0.46 |
| Lymphocytes + others | 23.9 | 23.3 | 20.3 | 22.4 | 14.0 | 24.1 | 20.5 | 16.6 | 3.3 | 0.53 | 0.12 | 0.31 |

[1] SEM = Standard Error of the Mean
[2] TRT = treatment

The proportion of monocytes decreased (P<0.001) and that of granulocytes increased (P<0.001) after drying-off. However, the chitosan treatments showed no effect relative to control on the proportions of these cell populations.

Expression of Immune Regulators

As the mammary gland immune system is activated, expression of immunoregulatory genes in mammary immune and epithelial cells increases. The cells produce and release proinflammatory cytokines that increase the bactericidal capacity of macrophages and neutrophils. Thus, measuring expression levels of key immunoregulatory genes by somatic cells can indicate the degree of activation of the mammary immune system.

The expression of key immunoregulatory genes by somatic cells was determined on d 1, 3, and 5 after the chitosan treatments. The genes investigated were CXCL8 [chemokine (C-X-C motif) ligand 8], CCL2 [chemokine (C-C motif) ligand 2], TNF (tumor necrosis factor), CD14 (CD14 molecule), and IL1β (*Bos taurus* interleukin 1 beta. The genes ACTB (actin, beta), GAPDH (glyceraldehyde-3-phosphate dehydrogenase), PPIA (peptidylprolyl isomerase A), and YWHAZ (tyrosine 3-monooxygenase/tryptophan 5-monooxygenase activation protein, zeta) were also selected for testing as potential housekeeping genes for the normalization of gene expression.

Skim milk and somatic cells were separated from milk and mammary secretion samples by centrifugation (1,000× g, 4° C., 20 min). Pelleted somatic cells were washed with 10 mL of phosphate-buffered saline (PBS) (Mediatech, Manassas, Va.) and centrifuged (500×g, 4° C., 10 min). The PBS was discarded, and the cell pellet was suspended in 250 µL of PBS. The samples were then stabilized in 1 mL of RNAlater™ solution (Sigma-Aldrich Co.) and stored at −80° C. prior to RNA extraction.

Total RNA was extracted from somatic cells (−80° C. samples) using the PureLink™ RNA Mini Kit and TRIzol™ RNA isolation reagents (Life Technologies, Carlsbad, Calif.) according to the manufacturer's instructions. The extraction process included on-column digestion with PureLink™ DNase (Life Technologies) to eliminate possible DNA contamination. The concentration and purity of the RNA were evaluated by spectrophotometric analysis using an ND-1000 spectrophotometer (NanoDrop Technologies Inc., Wilmington, Del.), and RNA integrity was assessed with an Agilent 2100 Bioanalyzer system (Agilent Technologies, Waldbronn, Germany) using an Agilent RNA 600 Nano kit (Agilent Technologies) according to the manufacturer's instructions. Samples containing less than 31.25 ng/µL were concentrated with RNA Clean & Concentrator™5 (Zymo Research, Irvine, Calif.) according to the manufacturer's protocol.

Reverse transcription was performed using TransScript™ First-Strand cDNA Synthesis Super Mix (TransGen Biotech, Beijing, China) according to the manufacturer's protocol. From the resulting cDNA, 3.5 µL of each sample was used to make a pool (116 samples). The remaining cDNA was diluted 1:15 in water. A mixture of 3 µL of cDNA, 5 µL of Fast SYBR™ Green PCR Master Mix (Applied Biosystems Inc., Foster City, Calif.), and 2 µL of primers (Applied Biosystems Inc.) was used for amplification and quantification. The primer concentrations are listed in Table 5.

TABLE 5

Primers used during real-time PCR

| Gene[1] | GenBank number[2] | Hybrid-ization | Primers (5'-3') | Primer conc.[3] (nM) | Amplicon length (bp) |
|---|---|---|---|---|---|
| ACTB | NM_173979[a] | F 1051 | TGGCACCCAGCACAA TGA (SEQ ID NO: 1) | 300 | 123 |
|  |  | R 1173 | CCTGCTTGCTGATCC ACATCT (SEQ ID NO: 2) | 300 |  |
| CCL2 | NM_174006[b] | F 222 | CCTAAAGAGGCTGTG ATTTTCAAGACC (SEQ ID NO: 3) | 300 | 142 |
|  |  | R 363 | TGGGTTGTGGAGTGA GTGCTC (SEQ ID NO: 4) | 50 |  |
| CD14 | NM_174008[b] | F 20 | AAAGAATCCACAGTC CAGCCGA (SEQ ID NO: 5) | 300 | 145 |
|  |  | R 164 | GCTCGCAGGGTTCTG TTGTG (SEQ ID NO: 6) | 50 |  |
| CXCL8 | NM_173925[a] | F 239 | GAGAGTGGGCCACAC TGTGAA (SEQ ID NO: 7) | 300 | 116 |
|  |  | R 354 | TTCACAAATACCTGC ACAACCTTCT (SEQ ID NO: 8) | 300 |  |
| GAPDH | NM_001034034[b] | F 513 | GCCTCCTGCACCACC AACT (SEQ ID NO: 9) | 300 | 113 |
|  |  | R 625 | TCTTCTGGGTGGCAG TGATG (SEQ ID NO: 10) | 50 |  |
| IL1β | NM_174093[a] | F 437 | AAACTCCAGGACAGA GAGCAAAA (SEQ ID NO: 11) | 300 | 126 |
|  |  | R 562 | CTCTCCTTGCACAAA GCTCATG (SEQ ID NO: 12) | 300 |  |

TABLE 5-continued

Primers used during real-time PCR

| Gene[1] | GenBank number[2] | Hybrid-ization | Primers (5'-3') | Primer conc.[3] (nM) | Amplicon length (bp) |
|---|---|---|---|---|---|
| PPIA | NM_178320[a] | F 317 | ATGCTGGCCCCAACA CAA (SEQ ID NO: 13) | 300 | 101 |
|  |  | R 417 | CCCTCTTTCACCTTG CCAAA (SEQ ID NO: 14) | 300 |  |
| TNF | NM_173966[a] | F 408 | GCCCTCTGGTTCAAA CACTCA (SEQ ID NO: 15) | 300 | 127 |
|  |  | R 534 | TGAGGGCATTGGCAT ACGA (SEQ ID NO: 16) | 50 |  |
| YWHAZ | NM_174814[a] | F 530 | AATGCAACCAACACA TCCTATCAG (SEQ ID NO: 17) | 300 | 131 |
|  |  | R 660 | GTTCAGCAATGGCTT CATCAAAT (SEQ ID NO: 18) | 300 |  |

[1] ACTB = actin, beta; CCL2 = chemokine (C-C motif) ligand 2; CD14 = CD14 molecule; CXCL8 = chemokine (C-X-C motif) ligand 8; GAPDH = glyceraldehyde-3-phosphate dehydrogenase; IL1β = Bos taurus interleukin 1 beta; PPIA = peptidylprolyl isomerase A; TNF = tumor necrosis factor; YWHAZ = tyrosine 3-monooxygenase/tryptophan 5-monooxygenase activation protein, zeta.
[2] Primers were either a) taken from Dudemaine et al. (2014) Anim. Genet. 45:629-640 or b) designed using the Ensembl gene browser (Yates et al., (2016), Nucleic Acids Res. 44:D710-D716) following the primer design of Brosseau et al. (2010) RNA 16:442-449.
[3] Primer concentrations ranging from 50 to 900 nM were tested during optimization reactions.

The PCR conditions consisted of denaturation at 95° C. for 20 s and then 40 cycles of amplification at 95° C. for 3 s and 60° C. for 30 s. The samples were quantified with standard curve experiments run on a StepOnePlus™ real-time PCR system (Applied Biosystems Inc.) using a standard curve derived from a serial dilution of the pool.

The genes ACTB, GAPDH, PPIA, and YWHAZ were tested using NormFinder™ software (Andersen et al., (2004), Cancer Res. 64:5245-5250). Expression of the PPIA and YWHAZ genes showed less variability between treatments, and those genes were therefore selected as the housekeeping genes. The normalized values were obtained from the ratio of the expression of the gene of interest to the geometric mean of the respective housekeeping genes.

The results are presented in Table 6. Data are presented as least squares means of $\log_{10}$-transformed values. Different letters indicate significant differences (P<0.05) among treatments.

TABLE 6

Normalized expression of somatic cell genes

| | | Normalized expression | | | | | P-value | | |
|---|---|---|---|---|---|---|---|---|---|
| Day | Gene | A | B | C | CTRL | SEM[1] | A + B + C vs. CTRL | C vs. A + B | B vs. A |
| 1 | CXCL8 | 0.69[a] | 0.61[a] | 1.03[a] | 0.07[b] | 0.10 | <0.001 | <0.01 | 0.61 |
|  | IL1β | 0.35[ab] | 0.57[a] | 0.75[a] | 0.27[b] | 0.11 | <0.01 | 0.06 | 0.21 |
|  | TNF | 0.48[a] | 0.34[b] | 0.74[a] | 0.12[b] | 0.09 | <0.001 | <0.01 | 0.25 |
|  | CCL2 | 0.43[b] | 0.31[b] | 0.79[a] | 0.17[b] | 0.08 | <0.01 | <0.01 | 0.41 |
|  | CD14 | 0.47[a] | 0.42[a] | 0.52[a] | 0.18[b] | 0.04 | <0.001 | 0.09 | 0.41 |
| 3 | CXCL8 | 0.29 | 0.34 | 0.32 | 0.3 | 0.10 | 0.88 | 0.98 | 0.75 |
|  | IL1β | 0.41 | 0.24 | 0.28 | 0.27 | 0.06 | 0.67 | 0.62 | 0.13 |
|  | TNF | 0.29[ab] | 0.31[ab] | 0.51[a] | 0.16[b] | 0.06 | <0.01 | <0.01 | 0.78 |
|  | CCL2 | 0.27 | 0.44 | 0.46 | 0.19 | 0.09 | 0.13 | 0.41 | 0.28 |
|  | CD14 | 0.37[ab] | 0.26[b] | 0.53[a] | 0.35[b] | 0.04 | 0.48 | <0.001 | 0.10 |
| 5 | CXCL8 | 0.32[a] | 0.19[b] | 0.25[b] | 0.08[b] | 0.07 | 0.02 | 0.96 | 0.14 |
|  | IL1β | 0.46[a] | 0.25[b] | 0.16[b] | 0.22[b] | 0.04 | 0.24 | <0.01 | <0.01 |
|  | TNF | 0.25 | 0.23 | 0.26 | 0.18 | 0.03 | 0.09 | 0.58 | 0.59 |
|  | CCL2 | 0.14 | 0.16 | 0.21 | 0.21 | 0.03 | 0.38 | 0.23 | 0.68 |
|  | CD14 | 0.27 | 0.23 | 0.23 | 0.32 | 0.03 | 0.08 | 0.61 | 0.42 |

[1] SEM = Standard Error of the Mean

A treatment×day interaction (P<0.01) was observed for the expression of all genes. Gene expression was greater on d 1 than on d 3 for CXCL8 (P<0.001), TNF (P=0.09), and IL1β (P=0.04). In comparison with d 5, gene expression on d 1 was greater (P<0.01) for CXCL8, CCL2, TNF, CD14, and IL1β. On d 1, the quarters treated with chitosan (treatments A, B and C) had greater expression of CXCL8 (P<0.001), CCL2 (P<0.01), TNF (P<0.001) CD14 (P<0.001), and IL1β (P<0.01) than the control quarters. On d 3, the quarters treated with chitosan had greater expression of TNF (P<0.01) than the control quarters. The quarters treated with chitosan (treatments A, B and C) had greater expression of CXCL8 (P=0.02), and tend to have greater expression of TNF (P=0.09), and CD14 (P=0.08) on d 5 in comparison with the control quarters. The quarters treated with the high viscosity chitosan (Treatment C) had greater expression of CXCL8 (P<0.01), CCL2 (P<0.01), TNF (P<0.01), CD14 (P=0.09), and IL1β (P=0.06) on d 1, of TNF (P<0.01) and CD14 (P<0.001) on d 3, and IL1β (P<0.01) on d 5 in comparison with the quarters treated with the low viscosity chitosan (Treatments A and B). The quarters treated with Treatment A (5 mL) had greater expression of IL1β (P<0.01) on d 5 than those treated with Treatment B (2.5 mL).

These results suggest that chitosan hydrogel infusion hastens mammary gland involution and causes a sustained influx of activated immune cells into the mammary gland which may reduce the risk of acquiring new intramammary infection during the drying-off period.

Example 8: Intramammary Infusion of Chitosan Hydrogels in Cows in Late Lactation in the Presence or Absence of a Teat Sealant Statistical Analysis Data were analyzed by ANOVA using the MIXED procedure of SAS™ software version 9.0 (SAS Institute Inc., Cary, N.C.) as a factorial design with chitosan and teat sealant as main factors. Time was used as a repeated effect, and sealant*chitosan(cow) was used as the subject. When variances were not homogeneous, data were $\log_{10}$-transformed prior to analyses. Differences were considered statistically significant when P≤0.05 and considered a trend when P<0.1.

Treatment of Animals and Sample Collection

Eight Holstein cows in late lactation (328±17 DIM at drying-off) producing more than 15 kg (average 20.5±1.1 kg) of milk per day were used. Cows were milked twice a day and projected or real 305 days milk production was 10,881±1359 kg. The group of cows was dried off at the same time, 62±4 days before expected calving date. Prior to dry-off (d −4), quarter SCC averaged 87,654±23,287 cell/mL.

At drying-off, each udder quarter was randomly assigned to 1 of 4 intramammary infusions, as follows: 5 mL of a 2% (w/v) hydrogel formulation of low-viscosity chitosan prepared as described in Example 7 (Treatment D; n=8), 4 g of Orbeseal™ teat sealant solution followed by 5 mL of a 2% (w/v) hydrogel formulation of low-viscosity chitosan (Treatment E; n=8), 4 g of Orbeseal™ teat sealant solution (Treatment F; n=8), or nonpyrogenic water (control; n=8).

Milk samples (200 mL) on d −4 and −1 and mammary secretions on d 5 and 10 were collected, prepared, stored and analyzed as described for Example 7.

Inflammatory Response

Inflammatory response was measured as in Example 7, and the results are shown in Table 7 below. Data are presented as least squares means±standard error of the least squares means.

TABLE 7

Average inflammation scores

| Period | Treatment | | | | P-value[1] | | |
|---|---|---|---|---|---|---|---|
| | D | E | F | CTRL | Seal | Chi | Seal × Chi |
| 0-24 h | 1.76 ± 0.14 | 1.55 ± 0.14 | 1.19 ± 0.18 | 1.25 ± 0.18 | 0.47 | <0.01 | 0.67 |
| 25-48 h | 1.30 ± 0.10 | 1.30 ± 0.10 | 1.45 ± 0.13 | 1.45 ± 0.13 | 1.00 | 0.14 | 1.00 |
| 49-170 h | 1.06 ± 0.06 | 1.11 ± 0.06 | 1.18 ± 0.07 | 1.08 ± 0.07 | 0.30 | 0.40 | 0.73 |

[1]Seal = treatments D + CTRL (no sealant) vs treatments E + F (including sealant)
Chi = treatments D + E (including chitosan) vs treatments F + CTRL (no chitosan)
Seal × Chi = treatments D + F (chitosan alone or sealant alone) vs treatments E + CTRL (sealant + chitosan, or neither chitosan nor sealant)

The udder quarter inflammation scores were increased (P<0.01) by chitosan (Treatments D and E) during the first period, from 0 to 24 h after the treatments (Table 7). Sealant did not have an effect or interact (P>0.1) with chitosan on inflammation scores. Neither sealant nor chitosan affected (P<0.1) inflammation scores after the first day.

Somatic Cell Counts

Somatic cell counts (SCC) were determined as in Example 7, and the results are shown in FIG. 8A. During the pretreatment period (on d −4 and −1), no differences were observed between the udder quarters for SCC. Additionally, in every quarter, SCC increased from the day of drying-off (d −1) to d 10 (P<0.001). Nevertheless, a chitosan×time interaction was observed for SCC (P<0.001). On d 5, milk from the chitosan-treated quarters had greater SCC (P<0.001) values than the quarters without chitosan. The infusion of sealant did not interact with chitosan or have an effect (P>0.1) on SCC.

Markers of Mammary Involution

Levels of BSA, LDH and lactoferrin are measured as in Example 7, and the results are shown in FIGS. 8B-D. For LDH activity, the intra- and interassay coefficients of variation were 2.3% and 4.8%, respectively; for BSA concentration, the intra- and interassay coefficients of variation were 1.1% and 3.1%, respectively; and for lactoferrin concentration, the intra- and interassay coefficients of variation were 4.5 and 6.3%, respectively.

During the pretreatment period (on d −4 and −1), no differences were observed between the udder quarters for any of BSA, LDH or lactoferrin levels. Additionally, in every quarter, BSA, LDH and lactoferrin levels increased from the day of drying-off (d −1) to d 10 (P<0.001). Nevertheless, a chitosan×time interaction was observed for BSA concentration (P<0.01), lactoferrin concentration (P=0.06) and LDH activity (P<0.001). On d 5, milk from the quarters treated with chitosan (Treatments D and E) had greater BSA (P<0.01), lactoferrin (P=0.001) and LDH (P<0.0001) values than the quarters not treated with chitosan (Treatment F and control). The infusion of sealant did not interact with chitosan or have an effect (P>0.1) on the levels of any of BSA, LDH or lactoferrin.

Identification of Somatic Cells by Flow Cytometry

The identification of somatic cells was carried out as for Example 7, except that seven-color immunophenotyping of somatic cells was performed on samples collected on d −1 and 5. The results are shown in Table 8. Data are presented as least squares means.

TABLE 8

Percentages of somatic cell types

| Cell type | Percentage of cells (%) Day −1 | | | | | Percentage of cells (%) Day 5 | | | | | P-value[1] | | | |
|---|---|---|---|---|---|---|---|---|---|---|---|---|---|---|
| | D | E | F | CTRL | SEM | D | E | F | CTRL | SEM | DAY | Seal | Chi | Seal × Chi |
| Monocytes | 27.9 | 32.0 | 35.9 | 30.3 | 4.4 | 17.1 | 17.3 | 26.2 | 17.5 | 3.3 | <0.001 | 0.07 | 0.12 | 0.31 |
| Granulocytes | 48.8 | 46.4 | 37.6 | 45.5 | 5.4 | 65.6 | 65.2 | 55.7 | 61.8 | 3.6 | <0.001 | 0.17 | 0.04 | 0.35 |
| Lymphocytes + others | 23.4 | 21.6 | 26.6 | 24.1 | 2.9 | 17.4 | 17.5 | 18.2 | 20.8 | 1.7 | <0.01 | 0.75 | 0.09 | 0.79 |

[1]Seal = treatments D + CTRL (no sealant) vs treatments E + F (including sealant)
Chi = treatments D + E (including chitosan) vs treatments F + CTRL (no chitosan)
Seal × Chi = treatments D + F (chitosan alone or sealant alone) vs treatments E + CTRL (sealant + chitosan, or neither chitosan nor sealant)

After drying-off, the proportions of monocytes ($P<0.001$) and lymphocytes plus other cell types ($P<0.01$) decreased. Conversely, the proportion of granulocytes increased ($P<0.001$) after drying-off. There was no effect of chitosan or teat sealant on the proportions of these cell populations.

Expression of Immune Regulators

Expression of key immune regulator genes by somatic cells on d 5 after treatment was carried out as for Example 7, except that GAPDH and YWHAZ were selected as the housekeeping genes. The results are shown in Table 9 below. Data are presented as least squares means of $\log_{10}$-transformed values. Different letters indicate significant differences ($P<0.05$) among treatments.

TABLE 9

Normalized expression of somatic cell genes

| Day | Gene | Treatments | | | | | P-value | | |
|---|---|---|---|---|---|---|---|---|---|
| | | D | E | F | CTRL | SEM | Seal | Chi | Seal × Chi |
| 5 | CXCL8 | $0.37^a$ | $0.42^a$ | $0.16^b$ | $0.14^b$ | 0.06 | 0.53 | <0.001 | 0.82 |
| | IL1β | $0.35^a$ | $0.35^a$ | $0.26^b$ | $0.20^b$ | 0.04 | 0.50 | <0.01 | 0.46 |
| | TNF | 0.22 | 0.21 | 0.21 | 0.13 | 0.04 | 0.28 | 0.17 | 0.21 |
| | CCL2 | $0.20^a$ | $0.26^a$ | $0.10^b$ | $0.09^b$ | 0.03 | 0.23 | <0.001 | 0.32 |
| | CD14 | 0.24 | 0.25 | 0.28 | 0.28 | 0.03 | 0.73 | 0.20 | 0.85 |

[1]Seal = treatments D + CTRL (no sealant) vs treatments E + F (including sealant)
Chi = treatments D + E (including chitosan) vs treatments F + CTRL (no chitosan)
Seal × Chi = treatments D + F (chitosan alone or sealant alone) vs treatments E + CTRL (sealant + chitosan, or neither chitosan nor sealant)

Treatment with chitosan (Treatments D and E) increased expression of the somatic cell genes CXCL8 ($P<0.001$), CCL2 ($P<0.001$), and IL1β ($P<0.01$). However, gene expression of TNF and CD14 was not affected by chitosan. The infusion of sealant did not interact with chitosan or have any effect ($P>0.1$) on any of these genes.

Thus, chitosan induced changes in involution markers and immune responses markers were not affected by the presence or absence of the teat sealant, showing that both approaches are fully compatible and could be used in combination.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

The invention claimed is:

1. A method of reducing the risk of intramammary infection in a lactating mammal at drying-off, the method comprising administering a composition to one or more teats of the lactating mammal, via intramammary infusion, the composition comprising a biological response modifier and an acceptable carrier, wherein the biological response modifier comprises a chitosan hydrogel, wherein the composition is free of antibiotics, and wherein the composition is effective to induce recruitment of immune cells into the teat cistern.

2. The method according to claim 1, wherein the lactating mammal is a bovine.

3. The method according to claim 1, wherein the chitosan hydrogel comprises chitosan and a weak base.

4. The method according to claim 3, wherein the chitosan has a degree of deacetylation greater than 90%.

5. The method according to claim 3, wherein the chitosan has a weight average molecular weight of from about 110 kD to about 250 kD.

6. The method according to claim 5, wherein the chitosan has a weight average molecular weight of from about 160 kD to about 170 kD.

7. The method according to claim 6, wherein the chitosan has a viscosity from about 90 cP to about 130 cP, when measured for a 1% solution of the chitosan in 1% acetic acid at 20° C.

8. The method according to claim 3, wherein the weak base has a $pK_a$ of from about 6 to about 7.

9. The method according to claim 3, wherein the weak base is β-glycerophosphate.

10. The method according to claim 3, wherein the chitosan hydrogel has a pH of 6.8.

11. A method of accelerating involution in a lactating mammal at drying-off, comprising administering a composition to one or more teats of the lactating mammal, via intramammary infusion, the composition comprising a biological response modifier and an acceptable carrier, wherein the biological response modifier comprises a chitosan hydrogel, wherein the composition is free of antibiotics and wherein the composition is effective to induce recruitment of immune cells into the teat cistern.

12. The method according to claim 11, wherein the lactating mammal is a bovine.

13. The method according to claim 11, wherein the chitosan hydrogel comprises chitosan and a weak base.

14. The method according to claim 13, wherein the chitosan has a degree of deacetylation greater than 90%.

15. The method according to claim 13, wherein the chitosan has a weight average molecular weight of from about 110 kD to about 250 kD.

16. The method according to claim 13, wherein the weak base has a $pK_a$ of from about 6 to about 7.

17. The method according to claim 13, wherein the chitosan hydrogel has a pH of 6.8.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: ACTB forward primer

<400> SEQUENCE: 1
tggcacccag cacaatga                                                       18

<210> SEQ ID NO 2
<211> LENGTH: 21
<212> TYPE: DNA
<213> ORGANISM: Artificial Sequence
<220> FEATURE:
<223> OTHER INFORMATION: ACTB reverse primer

<400> SEQUENCE: 2
cctgcttgct gatccacatc t                                                   21

<210> SEQ ID NO 3
<211> LENGTH: 27
<212> TYPE: DNA
<213> ORGANISM: Artificial Sequence
<220> FEATURE:
<223> OTHER INFORMATION: CCL2 forward primer

<400> SEQUENCE: 3
cctaaagagg ctgtgatttt caagacc                                             27

<210> SEQ ID NO 4
<211> LENGTH: 21
<212> TYPE: DNA
<213> ORGANISM: Artificial Sequence
<220> FEATURE:
<223> OTHER INFORMATION: CCL2 reverse primer

<400> SEQUENCE: 4
tgggttgtgg agtgagtgct c                                                   21

<210> SEQ ID NO 5
<211> LENGTH: 22
<212> TYPE: DNA
<213> ORGANISM: Artificial Sequence
<220> FEATURE:
<223> OTHER INFORMATION: CD14 forward primer

<400> SEQUENCE: 5
aaagaatcca cagtccagcc ga                                                  22

<210> SEQ ID NO 6
<211> LENGTH: 20
<212> TYPE: DNA
<213> ORGANISM: Artificial Sequence
<220> FEATURE:
<223> OTHER INFORMATION: CD14 reverse primer

<400> SEQUENCE: 6
gctcgcaggg ttctgttgtg                                                     20

<210> SEQ ID NO 7
<211> LENGTH: 21
<212> TYPE: DNA
<213> ORGANISM: Artificial Sequence

```
<220> FEATURE:
<223> OTHER INFORMATION: CXCL8 forward primer

<400> SEQUENCE: 7
gagagtgggc cacactgtga a                                      21

<210> SEQ ID NO 8
<211> LENGTH: 25
<212> TYPE: DNA
<213> ORGANISM: Artificial Sequence
<220> FEATURE:
<223> OTHER INFORMATION: CXCL8 reverse primer

<400> SEQUENCE: 8
ttcacaaata cctgcacaac cttct                                  25

<210> SEQ ID NO 9
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 9
gcctcctgca ccaccaact                                         19

<210> SEQ ID NO 10
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 10
tcttctgggt ggcagtgatg                                        20

<210> SEQ ID NO 11
<211> LENGTH: 23
<212> TYPE: DNA
<213> ORGANISM: Artificial Sequence
<220> FEATURE:
<223> OTHER INFORMATION: IL1beta forward primer

<400> SEQUENCE: 11
aaactccagg acagagagca aaa                                    23

<210> SEQ ID NO 12
<211> LENGTH: 22
<212> TYPE: DNA
<213> ORGANISM: Artificial Sequence
<220> FEATURE:
<223> OTHER INFORMATION: IL1beta reverse primer

<400> SEQUENCE: 12
ctctccttgc acaaagctca tg                                     22

<210> SEQ ID NO 13
<211> LENGTH: 18
<212> TYPE: DNA
<213> ORGANISM: Artificial Sequence
<220> FEATURE:
<223> OTHER INFORMATION: PPIA forward primer

<400> SEQUENCE: 13
atgctggccc caacacaa                                          18
```

```
<210> SEQ ID NO 14
<211> LENGTH: 20
<212> TYPE: DNA
<213> ORGANISM: Artificial Sequence
<220> FEATURE:
<223> OTHER INFORMATION: PPIA reverse primer

<400> SEQUENCE: 14
ccctctttca ccttgccaaa                                                    20

<210> SEQ ID NO 15
<211> LENGTH: 21
<212> TYPE: DNA
<213> ORGANISM: Artificial Sequence
<220> FEATURE:
<223> OTHER INFORMATION: TNF forward primer

<400> SEQUENCE: 15
gccctctggt tcaaacactc a                                                  21

<210> SEQ ID NO 16
<211> LENGTH: 19
<212> TYPE: DNA
<213> ORGANISM: Artificial Sequence
<220> FEATURE:
<223> OTHER INFORMATION: TNF reverse primer

<400> SEQUENCE: 16
tgagggcatt ggcatacga                                                     19

<210> SEQ ID NO 17
<211> LENGTH: 24
<212> TYPE: DNA
<213> ORGANISM: Artificial Sequence
<220> FEATURE:
<223> OTHER INFORMATION: YWHAZ forward primer

<400> SEQUENCE: 17
aatgcaacca acacatccta tcag                                               24

<210> SEQ ID NO 18
<211> LENGTH: 23
<212> TYPE: DNA
<213> ORGANISM: Artificial Sequence
<220> FEATURE:
<223> OTHER INFORMATION: YWHAZ reverse primer

<400> SEQUENCE: 18
gttcagcaat ggcttcatca aat                                                23
```